(12) United States Patent
Warlick

(10) Patent No.: US 11,844,739 B2
(45) Date of Patent: Dec. 19, 2023

(54) HANDHELD ACOUSTIC SHOCK WAVE OR PRESSURE PULSE APPLICATION DEVICE AND METHODS OF USE

(71) Applicant: SoftWave Tissue Regeneration Technologies, LLC, Woodstock, GA (US)

(72) Inventor: John F. Warlick, Woodstock, GA (US)

(73) Assignee: Softwave Tissue Regeneration Technologies, LLC, Woodstock, GA (US)

(*) Notice: Subject to any disclaimer, the term of this patent is extended or adjusted under 35 U.S.C. 154(b) by 246 days.

(21) Appl. No.: 17/533,680

(22) Filed: Nov. 23, 2021

(65) Prior Publication Data

US 2022/0079838 A1  Mar. 17, 2022

Related U.S. Application Data

(62) Division of application No. 16/367,989, filed on Mar. 28, 2019, now Pat. No. 11,311,454.

(51) Int. Cl.
*A61H 23/00* (2006.01)
*A61H 23/02* (2006.01)
(Continued)

(52) U.S. Cl.
CPC ..... *A61H 23/008* (2013.01); *A61B 17/22004* (2013.01); *A61B 17/225* (2013.01);
(Continued)

(58) Field of Classification Search
CPC ............ A61H 23/0245; A61H 23/0236; A61H 23/008; A61N 1/0472; A61N 1/048; A61N 7/00; A61N 7/02; A61N 2007/003; A61N 2007/0021; A61N 2007/0026; A61B 17/22; A61B 17/22004; A61B 8/00; A61B 1/00124; A61B 8/4272; A61B 8/4281; A61B 8/42; A61B 8/44; A61B 18/00
(Continued)

(56) References Cited

U.S. PATENT DOCUMENTS 3,848,607 A * 11/1974 St. Clair ................ A61F 7/123
                                                         392/471
6,186,963 B1   2/2001 Schwarze et al.
(Continued)

*Primary Examiner* — Justine R Yu
*Assistant Examiner* — Alexander Morales
(74) *Attorney, Agent, or Firm* — David L. King

(57) ABSTRACT

A handheld acoustic shock wave or pressure pulse applicator device has a body structure and an applicator head. The body structure has a proximal end and a distal end with a longitudinal axis extending between the ends. The applicator head is at the distal end. the head emits pressure pulses or shock waves at an inclined angle relative to the longitudinal axis of the body structure. The applicator head has a balloon or lens or membrane through which the emitted pressure pulses or shock waves pass. The lens or membrane is configured to be coupled directly or indirectly to an exposed soft tissue surface of a palate inside a patient's mouth to direct emitted pressure pulses or shock waves to the brain. The applicator device can be configured with the inclined obtuse angle fixed between 150 degrees and 90 degrees or can be adjustable between 180 degrees and 90 degrees.

15 Claims, 20 Drawing Sheets

(51) Int. Cl.
  *A61H 23/04* (2006.01)
  *A61N 7/00* (2006.01)
  *A61B 17/225* (2006.01)
  *A61B 17/22* (2006.01)
  *A61H 21/00* (2006.01)

(52) U.S. Cl.
  CPC ......... *A61H 21/00* (2013.01); *A61H 23/0236* (2013.01); *A61H 23/0245* (2013.01); *A61H 23/04* (2013.01); *A61N 7/00* (2013.01); *A61H 2201/0103* (2013.01); *A61H 2201/0107* (2013.01); *A61H 2201/018* (2013.01); *A61H 2201/0153* (2013.01); *A61H 2201/0188* (2013.01); *A61H 2201/0192* (2013.01); *A61H 2201/1409* (2013.01); *A61H 2201/5043* (2013.01); *A61H 2203/02* (2013.01); *A61H 2205/02* (2013.01); *A61N 2007/0021* (2013.01); *A61N 2007/0026* (2013.01)

(58) Field of Classification Search
  USPC ....................................................... 601/1–4
  See application file for complete search history.

(56) References Cited

U.S. PATENT DOCUMENTS

| | | | |
|---|---|---|---|
| 7,507,213 | B2 | 3/2009 | Schultheiss et al. |
| 7,544,171 | B2 | 6/2009 | Schaden et al. |
| 8,162,859 | B2 | 4/2012 | Schultheiss et al. |
| 9,579,247 | B2 * | 2/2017 | Juto .................. G16H 20/70 |
| 10,327,981 | B1 | 6/2019 | Ayotte |
| 2003/0176892 | A1 * | 9/2003 | Shalev .................. A61N 1/205 607/3 |
| 2003/0176898 | A1 * | 9/2003 | Gross .................. A61M 5/1723 607/54 |
| 2006/0089673 | A1 | 4/2006 | Schultheiss et al. |
| 2007/0016112 | A1 | 1/2007 | Schultheiss et al. |
| 2007/0083245 | A1 * | 4/2007 | Lamensdorf ....... A61N 1/36082 607/45 |
| 2007/0142753 | A1 | 6/2007 | Warlick et al. |
| 2007/0239086 | A1 | 10/2007 | Ewell et al. |
| 2010/0274161 | A1 | 10/2010 | Azhari |
| 2011/0034832 | A1 * | 2/2011 | Cioanta ........... A61B 17/22012 601/1 |
| 2011/0092781 | A1 * | 4/2011 | Gertner ................. A61B 18/14 600/407 |
| 2020/0383692 | A1 * | 12/2020 | Brouillette ....... A61B 17/22012 |

* cited by examiner

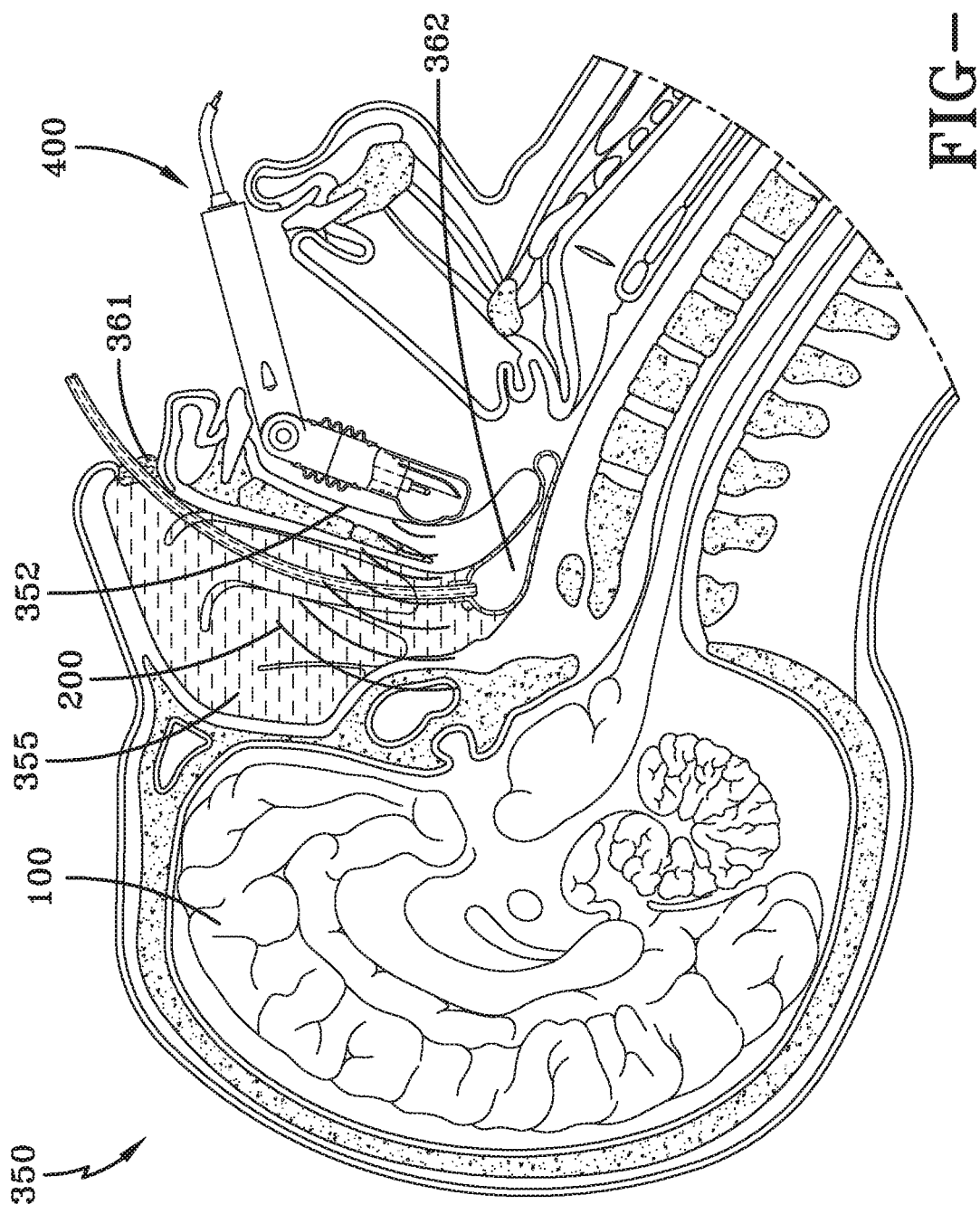

HANDHELD ACOUSTIC SHOCK WAVE OR PRESSURE PULSE APPLICATION DEVICE AND METHODS OF USE

RELATED APPLICATIONS

The present invention is a division of co-pending U.S. application Ser. No. 16/367,989 filed on Mar. 28, 2019 entitled, "Handheld Acoustic Shock Wave Or Pressure Pulse Application Device And Methods Of Use".

FIELD OF THE INVENTION

The present invention relates to a handheld device for delivering acoustic shock waves or pressure pulses to brain tissue non-invasively and methods used in conjunction with the device to treat the brain for a variety of disorders.

BACKGROUND OF THE INVENTION

In practice, the transmission of acoustic shock waves and pressure pulses works extremely well in fluids. The wave patterns can propagate quickly in fluids when not obstructed by solid objects or voids. If a solid object is in the path of the wave pattern, the wave energy is effectively blocked to a large extent with a small fraction passing through the object. Alternatively, if the wave patter propagates into a void or air gap, the energy is dissipated.

U.S. Pat. No. 7,507,213 B2, issued Mar. 24, 2009, entitled "Pressure Pulse/Shock Wave Therapy Method For Organs"; disclosed invasive procedures to treat organs such as the heart and the brain by surgically exposing the organ and invasively treating the organ with acoustic shock waves or pressure pulses after the surgical procedure to at least partially expose the organ or to provide a surgical access portal to the organ. The idea was to provide an unobstructed path to the tissue of the surgically exposed organ. The entire brain is shown exposed and being treated in FIG. 15 of this prior art patent, shown in the present application as Prior Art FIG. 13A.

The same group of inventors in U.S. Pat. No. 7,544,171 B2, issued Jun. 9, 2009, entitled "Methods For Promoting Nerve Regeneration And Neuronal Growth And Elongation"; proposed a variety of diseases associated with the brain could be treated non-invasively as illustrated in FIG. 13 of that prior art patent, shown in the present application as Prior Art FIG. 13B. That patent suggested and taught that transmission of the shock waves or pressure pulses could effectively pass through the hard skull bone to treat the underlying brain tissue. The inventors were confident that the beneficial therapy could be useful for a variety of brain disorders. These inventors, while believing the benefits of such treatments were potentially great, had provided two less than ideal solutions. The first requiring invasive surgery provided a superior access. The second being non-invasive was simpler, but highly unpredictable as to what amount, if any, of the wave transmissions were getting through the bone to the brain. Since the bone thickness and hardness of the skull varies greatly, the energy passing through it is highly unpredictable. Overcoming this uncertainty by increasing the energy levels to higher levels increases the risk of brain trauma caused by the treatment.

The present invention, as described below, overcomes all these prior art deficiencies by employing a novel handheld application device that can be used non-invasively without any surgical access, but while transmitting the pressure pulses or acoustic waves, while completely avoiding the thick bone structure of the skull.

SUMMARY OF THE INVENTION

A handheld acoustic shock wave or pressure pulse applicator device has a body structure and an applicator head. The body structure has a proximal end and a distal end with a longitudinal axis extending between the ends. The applicator head is at the distal end. The head emits pressure pulses or shock waves at an inclined angle relative to the longitudinal axis of the body structure. The applicator head has a balloon or lens or membrane through which the emitted pressure pulses or shock waves pass. The lens or membrane is configured to be coupled directly or indirectly to an exposed soft tissue surface of a palate inside a patient's mouth to direct emitted pressure pulses or shock waves to the brain. The applicator device can be configured with the inclined angle being obtuse fixed between 150 degrees and 90 degrees. Alternatively, the inclined angle can be adjustable between 180 degrees and 90 degrees.

The shock wave head generates shock wave by either electrohydraulic, electromagnetic, piezoelectric or ballistic wave emissions. The applicator device of one embodiment further has a light for direct viewing. The applicator device further may have an optical viewing means connected to the device coupled to a monitor for viewing. The applicator device or parts thereof can be disposable after a single use. In one embodiment, the device includes replaceable electrodes or tips for refurbishing the device after use. The applicator device can have two fixed electrodes which are not adjustable and are pre-set at fixed gaps. Alternatively, the applicator device can have one or more adjustable electrodes. The adjustable electrodes include one or more adjustment means, the means being magnets, piezo ceramic or motors with gear boxes, pneumatic or hydraulic to change the tip distance.

The applicator device further may have a reflector. The reflector can be a generalized paraboloid, or the reflector can be an ellipsoid. The applicator device can have the wave emissions be focused, divergent, convergent, radial, spherical or unfocused waves. The wave emissions also can be transmitted at high energy or low energy.

The device of the present invention allows for a method of treating a brain using pressure pulses or shock waves. The method has the steps of inserting an applicator head of an acoustic shock wave or pressure pulse generator or source inside a mouth; coupling the applicator head directly or indirectly to an exposed surface of the palate; and activating the generator or source to emit pressure pulses or acoustic shock waves through the palate to the brain.

The method further can include the step of filling the nasal sinus cavities with fluid. This is accomplished by plugging or otherwise sealing said nasal sinus cavities to prevent fluid drainage while allowing the patient to breathe through the mouth. Preferably, the emitted pressure pulses or acoustic shock waves are transmitted in a pattern passing through the fluid filled nasal sinus cavities to the brain. The method allows the emitted pressure pulses or acoustic shock waves pattern to impinge the brain prior to the boney structure of the cranium or skull. The method has the pressure pulse being an acoustic pulse which includes several cycles of positive and negative pressure. The pressure pulse has an amplitude of the positive part of such a cycle should be above 0.1 MPa and the time duration of the pressure pulse is from below a microsecond to about a second. The rise times of the positive part of the first pressure cycle in the range of nano-seconds (ns) up to some milli-seconds (ms). The pressure pulse can be the acoustic shock waves of very fast pressure pulses having amplitudes above 0.1 MPa and rise times of the amplitude being below 1000 ns. Typically, the duration of the shock wave is typically below 1-3 micro-seconds (µs) for the positive part of a cycle and typically above some micro-seconds for the negative part of a cycle.

One treatment method features subjecting the brain to convergent, divergent, planar or near planar acoustic shock waves or pressure pulses in the absence of a focal point impinging the neuronal cells stimulating a cellular response in the absence of creating cavitation bubbles evidenced by not experiencing the sensation of hemorrhaging caused by the emitted waves or pulses in neuronal cells wherein the neuronal cells are positioned within an unobstructed path of the emitted shock waves or pressure pulses; and away from any localized geometric focal volume or point of the emitted shock waves wherein the emitted shock waves or pressure pulses either have no geometric focal volume or point or have a focal volume or point ahead of the neuronal cells or beyond the neuronal cells thereby passing the emitted waves or pulses through the neuronal cells while avoiding having any localized focal point within the neuronal cells of the brain.

Ideally, the emitted pressure pulses or shock waves are convergent, divergent, planar or near planar and the pressure pulse shock wave generator or source is based on electrohydraulic, electromagnetic, piezoceramic or ballistic wave generation having an energy density value ranging as low as $0.00001$ mJ/mm$^2$ to a high end of below $1.0$ mJ/mm$^2$.

The method allows for subjecting the brain directly to the acoustic shock waves with a low energy density of less than $1.0$ mJ/mm$^2$ per shock wave to stimulate said neuronal cells or brain tissue wherein the neuronal cells or brain tissue is positioned directly within a path of the emitted pressure pulses or acoustic shock waves in the absence of any focal point or if a focal point exists, the neuronal cells or brain tissue being treated is positioned away from any focal point.

The method allows the energy density to be selected to avoid any cell damage to the neuronal cells or brain tissue. The method beneficially treats the brain to stimulate by accelerating or increasing neuronal cell growth or regeneration wherein the administering is applied to a patient who has a pathological condition of the brain exhibiting damage caused by injury or disease such as diabetes, brain damage associated with stroke, or for the treatment of neurological disorders related to neurodegeneration, including Parkinson's disease, Alzheimer's disease and amyotrophic lateral sclerosis, multiple sclerosis and disseminated sclerosis, or for the treatment of mental disorders including bipolar disorder, depression, and schizophrenia. The method of treating the brain stimulates the brain by accelerating and increasing neuronal cell neurological brain tissue growth or regeneration or repair and wherein the neuronal cell or neurological brain tissue is from a mammal which is a human or an animal.

Definitions

"Adrenergic receptor", the adrenergic receptors or adrenoceptors are a class of G protein-coupled receptors that are targets of many catecholamines like norepinephrine (noradrenaline) and epinephrine (adrenaline) produced by the body, but also many medications like beta blockers, $\beta 2$ agonists and $\alpha 2$ agonists, which are used to treat high blood pressure and asthma for example. Many cells have these receptors, and the binding of a catecholamine to the receptor will generally stimulate the sympathetic nervous system (SNS). SNS is responsible for the fight-or-flight response, which is triggered for example by exercise or fear causing situations. This response dilates pupils, increases heart rate, mobilizes energy, and diverts blood flow from non-essential organs to skeletal muscle. These effects together tend to increase physical performance momentarily.

Brain-derived neurotrophic factor, also known as BDNF, is a protein that, in humans, is encoded by the BDNF Gene. BDNF is a member of the neurotrophin family of growth factors, which are related to the canonical nerve growth factor. Neurotrophic factors are found in the brain and the periphery.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"Eosinophils", sometimes called eosinophiles or, less commonly, acidophils, area variety of white blood cells and one of the immune system components responsible for combating multicellular parasites and certain infections in vertebrates. Along with mast cells and basophils, they also control mechanisms associated with allergy and asthma. They are granulocytes that develop during hematopoiesis in the bone marrow before migrating into blood, after which they are terminally differentiated and do not multiply.

"Extracorporeal" means occurring or based outside the living body.

A "generalized paraboloid" according to the present invention is also a three-dimensional bowl. In two dimensions (in Cartesian coordinates, x and y) the formula yn=2px [with n being ≠2, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

"Paraboloid" according to the present invention is a three-dimensional reflecting bowl. In two dimensions (in Cartesian coordinates, x and y) the formula y2=2px, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude can be below 1000 ns, preferably at or below 100 ns. The duration of a shock wave is typically below 1-3 micro-seconds (μs) for the positive part of a cycle and typically above some micro-seconds for the negative part of a cycle.

"Shock Wave": As used herein is defined by Camilo Perez, Hong Chen, and Thomas J. Matula; Center for Industrial and Medical Ultrasound, Applied Physics Laboratory, University of Washington, 1013 NE 40th Street, Seattle, Washington 98105; Maria Karzova and Vera A. Khokhlovab; Department of Acoustics, Faculty of Physics, Moscow State University, Moscow 119991, Russia; (Received 9 October 2012; revised16 April 2013; accepted 1 May 2013) in their publication, "Acoustic field characterization of the Duolith: Measurements and modeling of a clinical shock wave therapy device"; incorporated by reference herein in its entirety.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which:

FIGS. 14A-14E are cross sectional plan views showing a treatment according to the present invention wherein the device of the present invention is inserted into the mouth in various locations and orientations.

DETAILED DESCRIPTION OF THE INVENTION

The present invention relates to the use of various therapeutic pressure pulse wave patterns or acoustic shock wave patterns as illustrated in FIGS. 1-12 for treating nerve damage or various neurological diseases or conditions of the brain or for preventing such conditions from occurring. Each illustrated wave pattern as discussed is applicable and useable with the handheld applicator of the present invention. The use of each of the different wave patterns has particularly interesting beneficial features that area remarkably valuable new tool in the fight against such diseases, particularly those of a degenerative non-reversible condition.

Prior to discussing the applicator device of the present invention, the FIGS. 1A-12 provide a detailed description of how the various types of wave patterns are created.

Figure 1A:
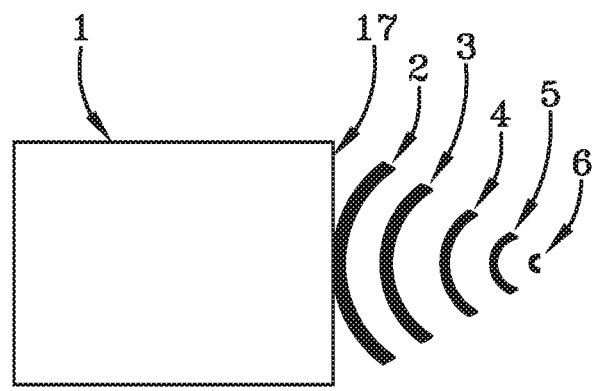
FIG. 1A is a simplified depiction of a pressure pulse/shock wave (PP/SW)generator with focusing wave characteristics.

FIG. 1A is a simplified depiction of a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The affected tissue or organ is generally located in or near the focal point which is located in or near position 6. At position 17 a water cushion or any other kind of exit window for the acoustical energy is located.

Figure 1B:
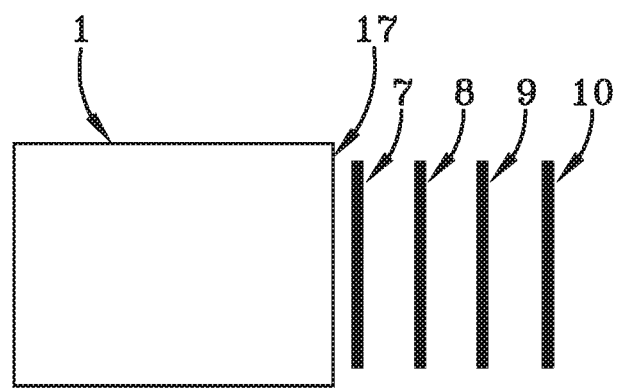
FIG. 1B is a simplified depiction of a pressure pulse/shock wave generator with plane wave characteristics.

FIG. 1B is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 1C:
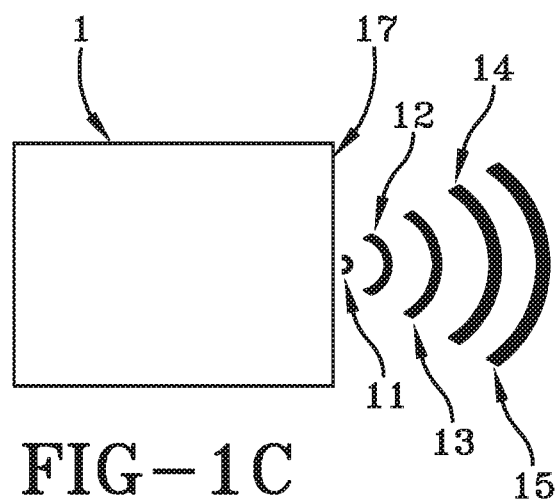
FIG. 1C is a simplified depiction of a pressure pulse/shock wave generator with divergent wave characteristics.

FIG. 1C is a simplified depiction of a pressure pulse/shock wave generator (shock wave head) with divergent wave characteristics. The divergent wave fronts maybe leaving the exit window 17 at point 11 where the amplitude of the wave front is very high. This point 17 could be regarded as the source point for the pressure pulses. In FIG. 1C the pressure pulse source may be a point source, that is, the pressure pulse may be generated by an electrical discharge of an electrode under water between electrode tips. However, the pressure pulse may also be generated, for example, by an explosion, referred to as a ballistic pressure pulse. The divergent characteristics of the wave front may be a consequence of the mechanical setup shown in FIG. 2B.

Figure 2A:
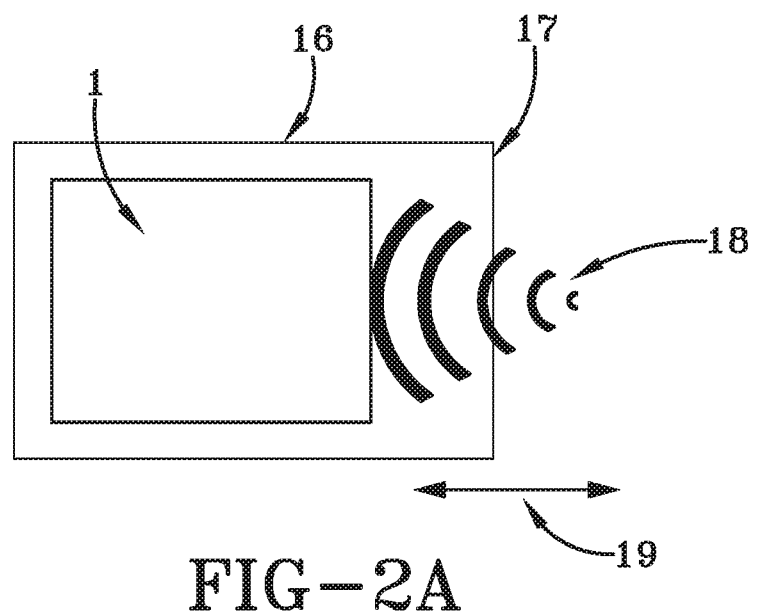
FIG. 2A is a simplified depiction of a pressure pulse/shock wave generator having an adjustable exit window along the pressure wave path. The exit window is shown in a focusing position.

FIG. 2A is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2A is similar to FIG. 1A but depicts an outer housing (16) in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 2A shows the situation in which the arrangement transmits focused pressure pulses.

Figure 2B:
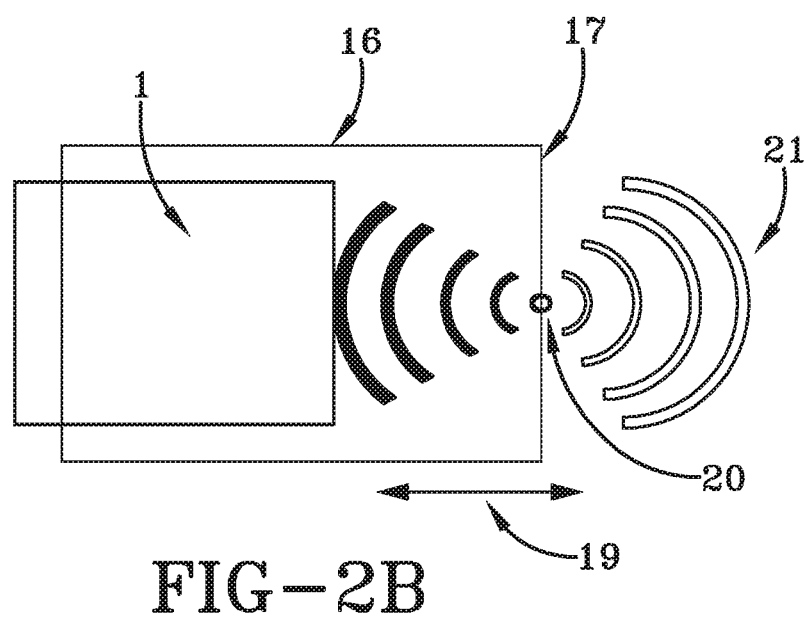
FIG. 2B is a simplified depiction of a pressure pulse/shock wave generator having an exit window along the pressure wave path. The exit window as shown is positioned at the highest energy divergent position.

FIG. 2B is a simplified depiction of the pressure pulse/shock wave generator (shock wave head) having an adjustable or exchangeable housing around the pressure wave path with the exit window 17 being in the highest energy divergent position. The configuration shown in FIG. 2B can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 2C:
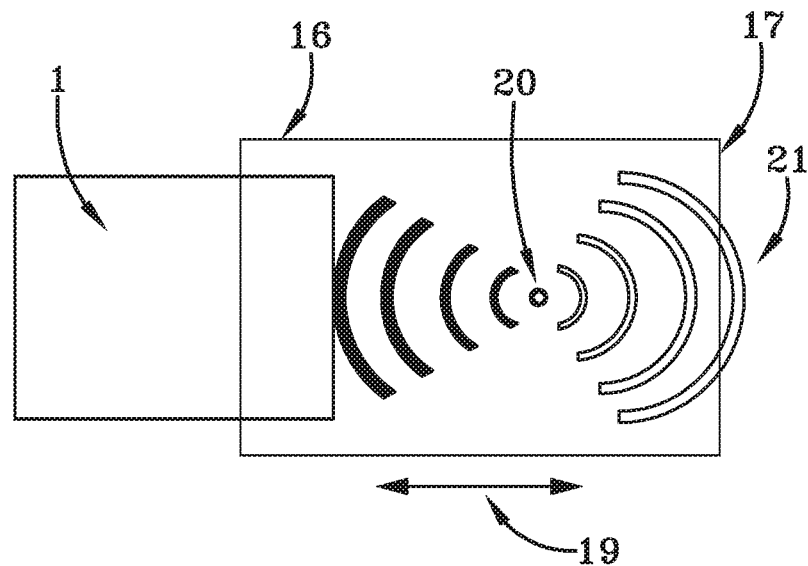
FIG. 2C is a simplified depiction of a pressure pulse/shock wave generator having an exit window along the pressure wave path. The exit window is shown at a low energy divergent position.

FIG. 2C is a simplified depiction of the pressure pulse/shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a patient's body. Thus, an appropriate adjustment can change the energy density of a wavefront without changing its characteristic.

This apparatus may, in certain embodiments, be adjusted/modified/or the complete shock wave head or part of it may be exchanged so that the desired and/or optimal acoustic profile such as one having wave fronts with focused, planar, nearly plane, convergent or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above-described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in the drawings are independent of the generation principle and thus are valid for not only electrohydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 3:
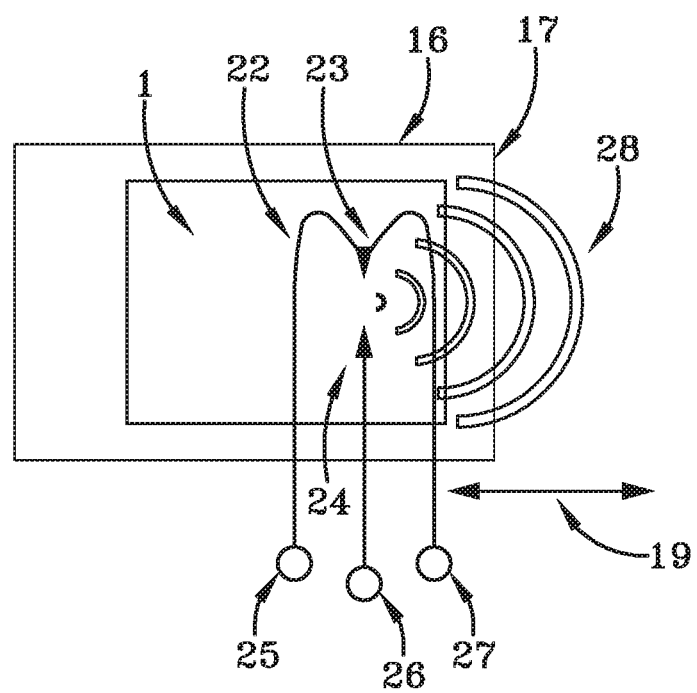
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves (28) behind the ignition point defined by a spark between the tips of the electrode (23, 24).

Figure 4A:
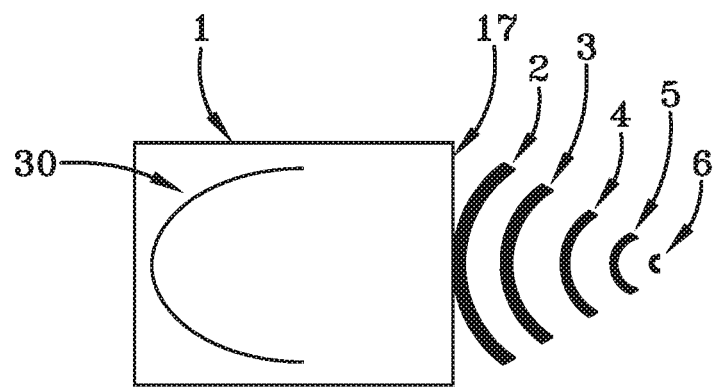
FIG. 4A is a simplified depiction of a pressure pulse/shock wave generator having a focusing element in the form of an ellipsoid. The waves generated are focused.

FIG. 4A is a simplified depiction of the pressure pulse/shock wave generator (shock wave head) having as focusing element an ellipsoid (30). Thus, the generated waves are focused at (6).

Figure 4B:
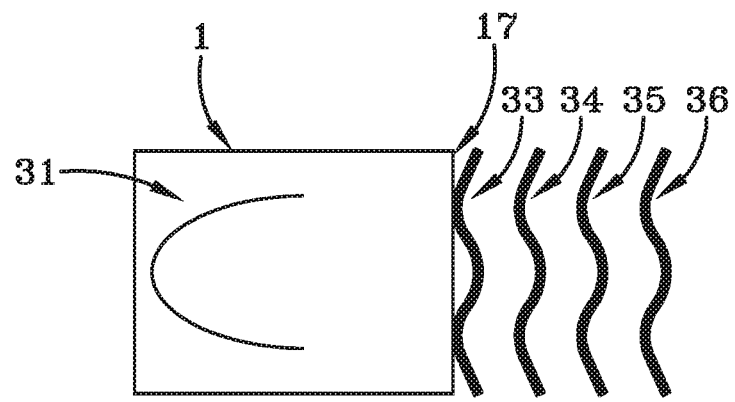
FIG. 4B is a simplified depiction of a pressure pulse/shock wave generator having a parabolic reflector element and generating waves that are disturbed plane.

FIG. 4B is a simplified depiction of the pressure pulse/shock wave generator (shock wave head) having as a focusing element an paraboloid ($y^2=2px$). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
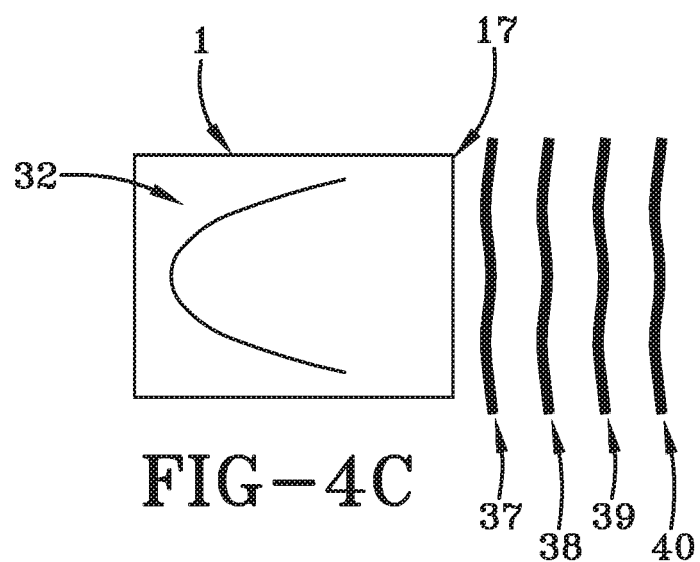
FIG. 4C is a simplified depiction of a pressure pulse I shock wave generator having a quasi parabolic reflector element (generalized paraboloid) and generating waves that are nearly plane/have nearly plane characteristics.

FIG. 4C is a simplified depiction of the pressure pulse/shock wave generator (shock wave head) having as a focusing element a generalized paraboloid ($y^n=2px$, with $1.2<n<2.8$ and $n \neq 2$). Thus, the characteristics of the wave fronts generated behind the exit window (37, 38, 39, and 40) are, compared to the wave fronts generated by a paraboloid ($y^2=2px$), less disturbed, that is, nearly plane (or nearly parallel or nearly even (37, 38, 39, 40)). Thus, conformational adjustments of a regular paraboloid ($y^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with $p=1.25$, introduction of a new electrode may result in p being about 1.05. If an electrode is used that adjusts itself to maintain the distance between the electrode tips ("adjustable electrode") and assuming that the electrodes burn down is 4 mm ($z=4$ mm), p will increase to about 1.45. To compensate for this burn down, and here the change of p, and to generate nearly plane wave fronts over the life span of an electrode, a generalized paraboloid having, for example $n=1.66$ or $n=2.5$ may be used. An adjustable electrode is, for example, disclosed in U.S. Pat. No. 6,217,531.

Figure 4D:
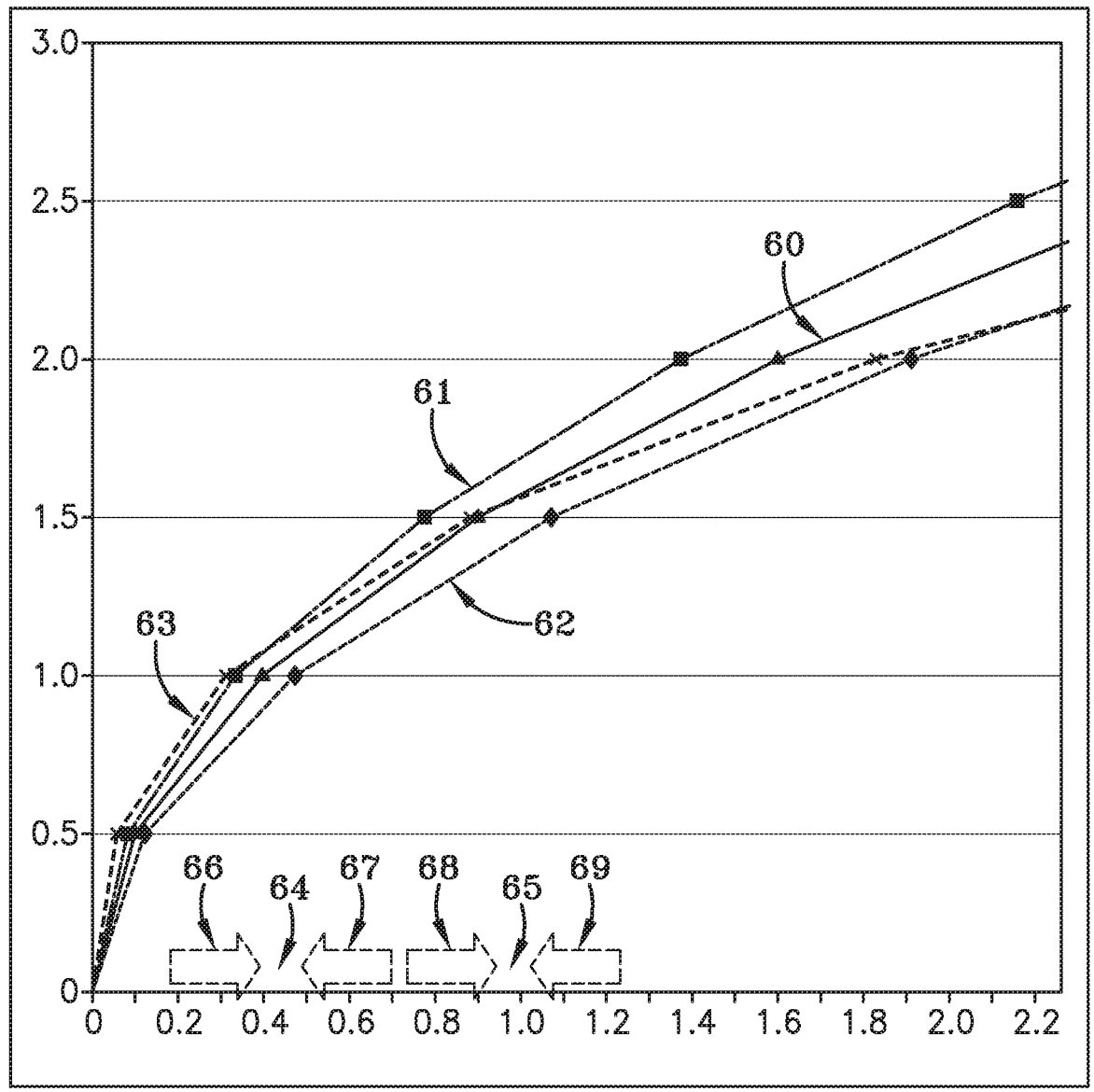
FIG. 4D is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4D shows sectional views of a number of paraboloids. Numeral 62 indicates a paraboloid of the shape $y^2=2px$ with $p=0.9$ as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. This value for the burned down electrode is indicated by 65 as $p/2=1$. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which $p=1.25$ cm. A generalized paraboloid is indicated by dashed line 63 and constitutes a paraboloid having a shape between paraboloids 61 and 62. This particular generalized paraboloid was generated by choosing a value of $n \neq 2$ and a p value of about 1.55 cm. The generalized paraboloid compensates for different p values that result from the electrode burn down and/or adjustment of the electrode tips.

Figure 5:
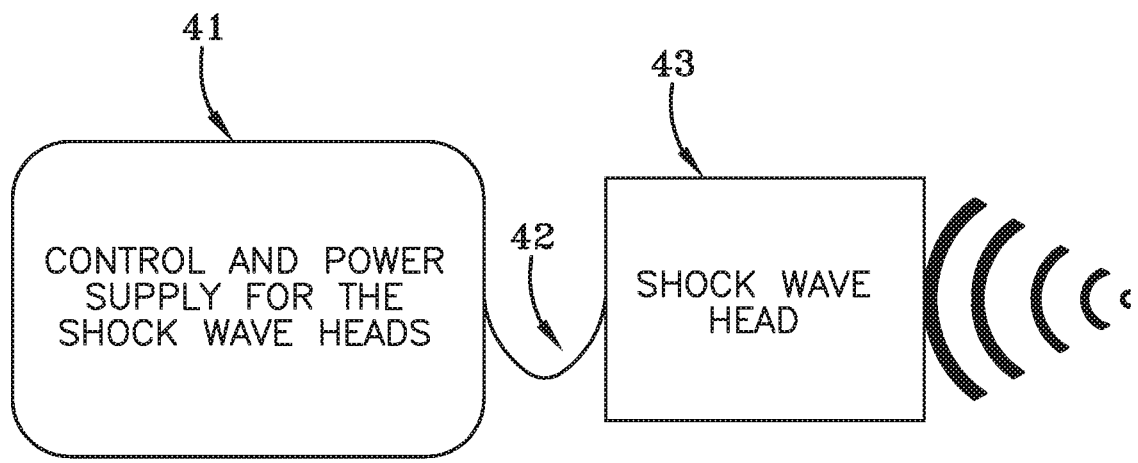
FIG. 5 is a simplified depiction of a pressure pulse/shock wave generator being connected to a control/power supply unit.

FIG. 5 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
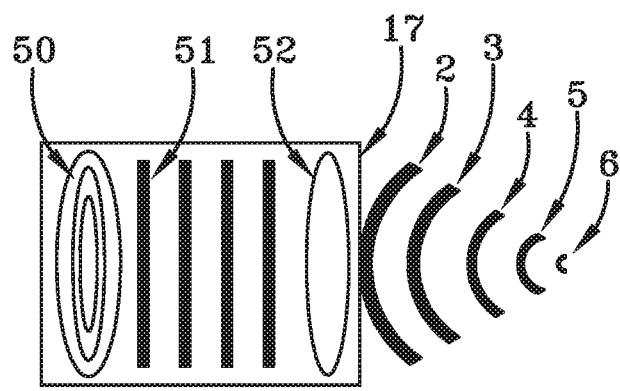
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
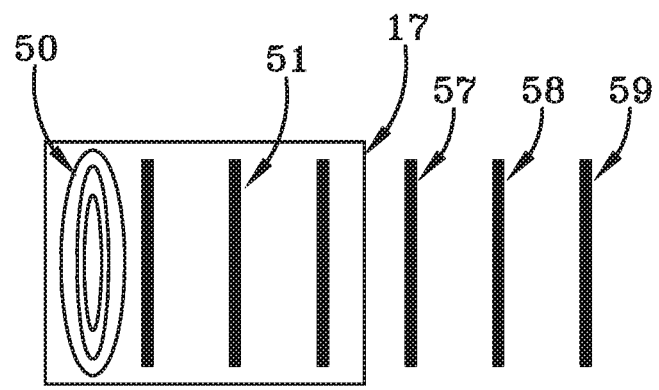
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
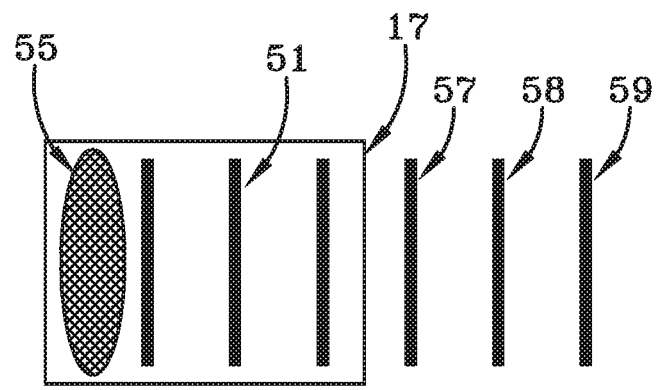
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
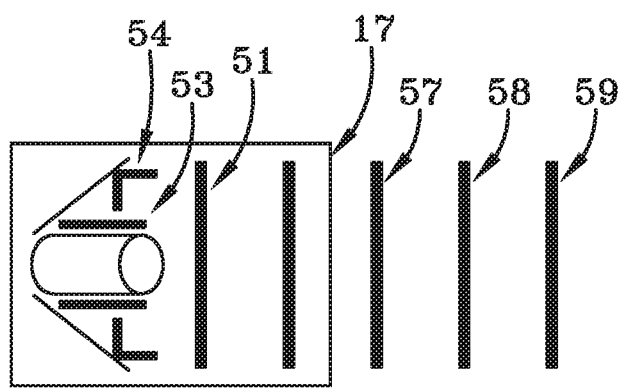
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
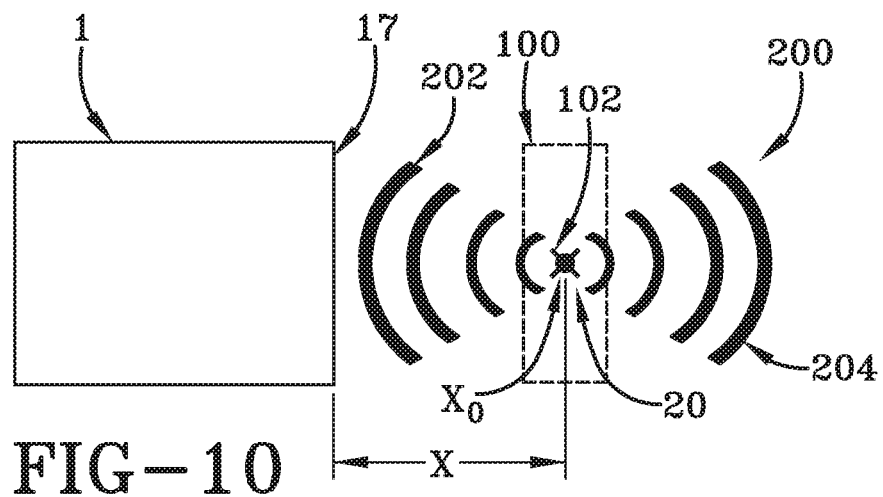
FIG. 10 is a simplified depiction of a pressure pulse/shock wave (PP/SW) generator with focusing wave characteristics shown focused with the focal point or geometrical focal volume being on an organ, the focus being targeted on the location $X_0$.
Figure 11:
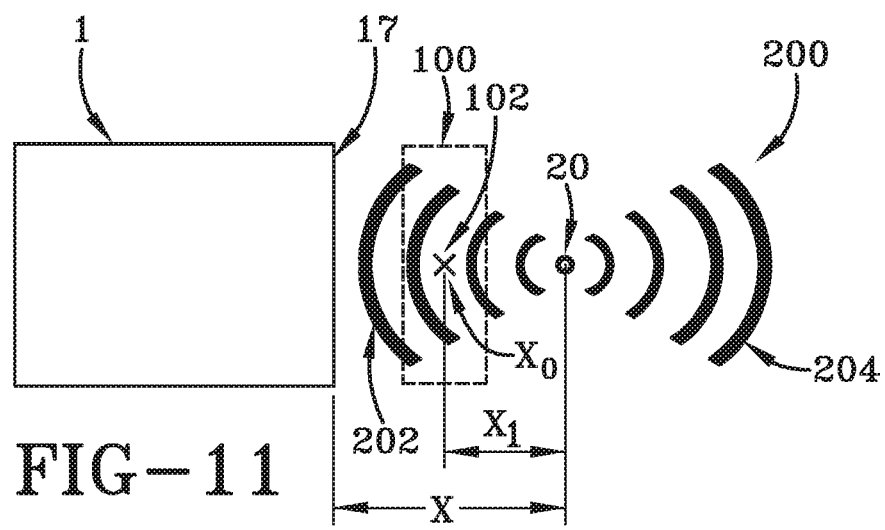
FIG. 11 is a simplified depiction of a pressure pulse/shock wave (PP/SW) generator with the focusing wave characteristics shown wherein the focus is located a distance X, from the location $X_0$ of an organ wherein the converging waves impinge the organ.
Figure 12:
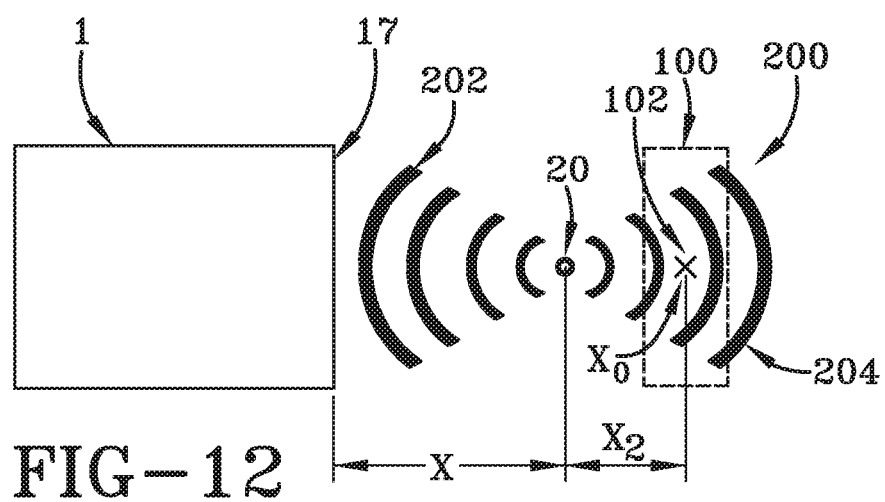
FIG. 12 is a simplified depiction of a pressure pulse/shock wave (PP/SW) generator with focusing wave characteristics shown wherein the focus is located a distance $X_2$ from the mass location $X_0$ wherein the emitted divergent waves impinge the organ.

With reference to FIGS. 10, 11 and 12 a schematic view of a shock wave generator or source 1 is shown emitting a shock wave front 200 from an exit window 17. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to FIG. 10 a tissue 100 is shown generally centered on the focal point or volume 20 at a location $X_0$ within the tissue 100. In this orientation the emitted waves are focused and thus are emitting a high intensity acoustic energy at the location $X_0$. This location $X_0$ can be anywhere within or on the organ. Assuming the tissue 100 is a brain tissue having a tumorous mass 102 at location $X_0$ then the focus is located directly on the mass 102. In one method of treating an infection or mass 102 these focused waves can be directed to destroy or otherwise reduce the mass 102 by weakening the outer barrier shield of the mass 102.

With reference to FIG. 11, the tissue 100 is shifted a distance X toward the generator or source 1. The tissue 100 at location $X_0$ being positioned a distance $X-X_1$ from the source 1. This insures the tissue 100 is impinged by converging waves 202 but removed from the focal point 20. When the tissue 100 is tissue this bombardment of converging waves 202 stimulates the cells activating the desired healing response as previously discussed.

With reference to FIG. 12, the tissue 100 is shown shifted or located in the diverging wave portion 204 of the wave front 200. As shown $X_0$ is now at a distance $X_2$ from the focal point or geometric volume 20 located at a distance X from the source 1. Accordingly, $X_0$ is located a distance $X+X_2$ from the source 1. As in FIG. 10 this region of diverging waves 204 can be used to stimulate the tissue 100 which when the tissue is a cellular tissue stimulates the cells to produce the desired healing effect or response.

Heretofore invasive techniques were not used in combination with shock wave therapy primarily because the shock waves were believed to be able to sufficiently pass through interfering body tissue to achieve the desired result in a non-invasive fashion. While this may be true, in many cases if the degenerative process is such that an operation is required then the combination of an operation in conjunction with shock wave therapy only enhances the therapeutic values and the healing process of the patient and the infected organ such that regenerative conditions can be achieved that would include not only revascularization of neurological tissue, but also the heart or other organs wherein sufficient or insufficient blood flow is occurring but also to enhance the improvement of ischemic tissue that may be occupying a portion of the infected tissue or organ. This ischemic tissue can then be minimized by the regenerative process of using shock wave therapy in the fashion described above to permit the tissue to rebuild itself in the region that has been afflicted.

As shown in FIGS. 1-12 the use of these various acoustic shock wave forms can be used separately or in combination to achieve the desired therapeutic effect of destroying a mass 102 or regenerating brain tissue growth or neurological cells.

Figure 13A:
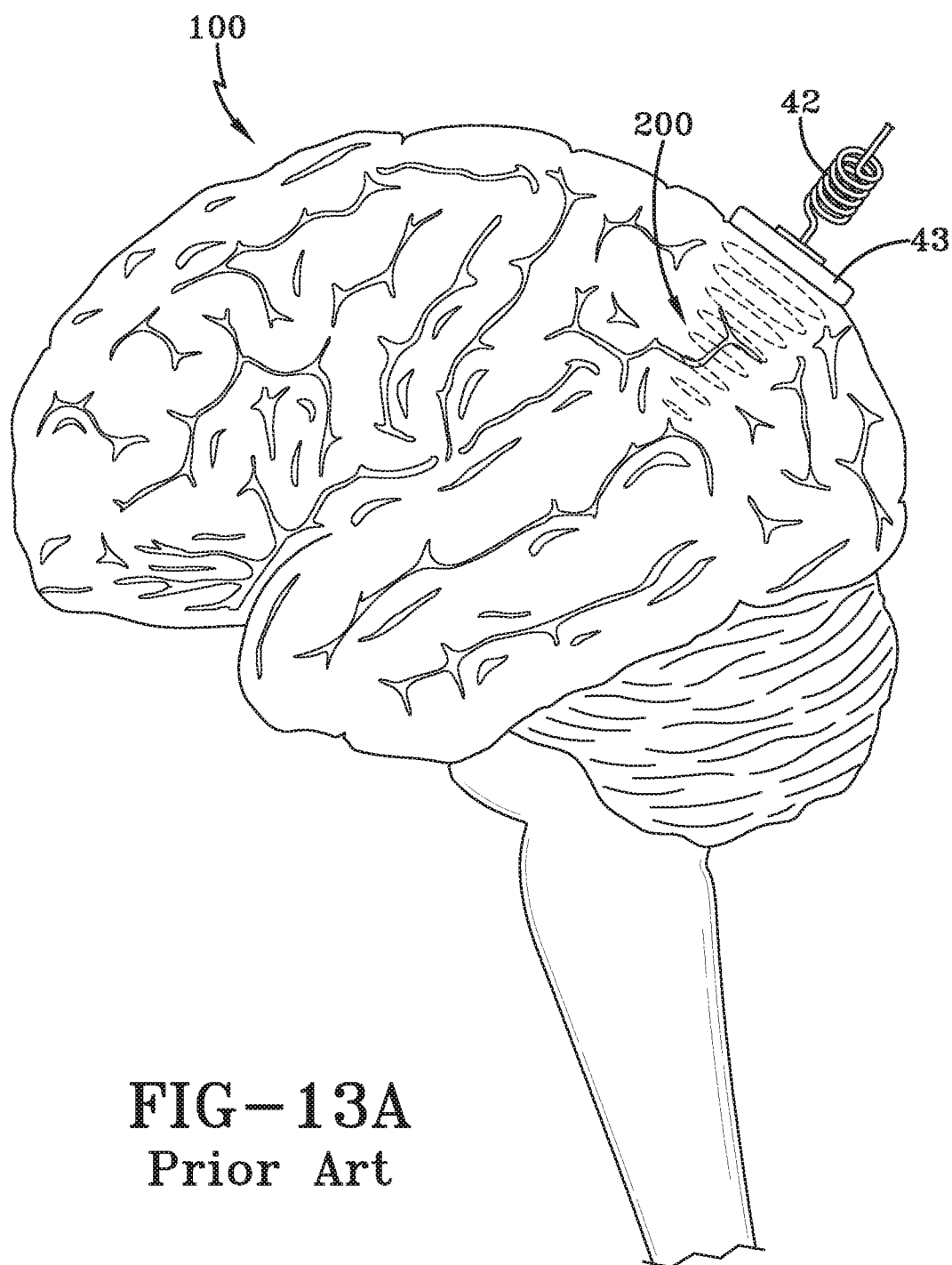
FIG. 13A is a perspective view of a brain being shock wave treated according to a prior art invasive method requiring a surgical procedure.
Figure 13B:
FIG. 13B shows a patient being treated extracorporeally according to another prior art method with shock waves being transmitted through the skin and cranial bone tissue to the neurological region to be treated.

With reference to FIGS. 13A, a perspective view of a portion of the treatment region 200 is shown. The neurological tissue 100, more commonly referred to as the brain 100, is the principal source of neurological activity. FIG. 13A was an invasive approach requiring a surgical access port or other exposure of the brain according to a prior art concept. In FIG. 13B, a non-invasive approach was contemplated requiring the wave to pass through the skulls boney structure.

Shock waves are a completely different technology and a quantum leap beyond other forms of neurological treatments. The mechanism of shock waves is far from being understood but is known to cause new blood vessels to grow in an area of treatment and regenerate bony tissue. In the present invention shock waves are used to treat nerve damage or neurological disease by regenerating or repairing the neurological tissue or nerve architecture to be regenerated. This is a phenomenal advancement in the current approach which includes difficult surgery. If surgery could be replaced in many cases, it would save millions of dollars, gain wide acceptance (non-invasive) and be a tremendous benefit to patients worldwide. Both prior art techniques were fraught with complications the invasive technique has all the risk associated with brain surgery and the early non-invasive approach thorough the skull simply was unpredictable as to how much wave energy actually reached the neural tissue of the brain.

The present invention as shown in an exemplary embodiment in FIGS. 14A-18 employs the use of pressure pulses or shock waves to stimulate a neuron or cellular nerve response stimulating a tissue regenerative healing process that activates the tissue or nerve cells surrounding the damaged nerves as well as the damaged nerves or neurons to initiate a systemic healing process within the brain.

In the pressure pulse or shock wave method of treating a tissue, an organ or the entire body of a host be it mechanical system or a mammal, the host system or mammal be it human or an animal with a risk of degenerative neurological or nerve damage or post-occurrence of such damage requires the host patient to be positioned in a convenient orientation to permit the source of the emitted waves to most directly send the waves to the target site to initiate pressure pulse or shock wave stimulation of the target area or zone with minimal, preferably with little or no obstructing features in the path of the emitting source or lens. Assuming the treatment region is accessible through an open access region then the shock wave applicator head 440 can be inserted and placed directly inside the mouth adjacent to the treatment region 200 providing a relatively unobstructed soft tissue path to the brain 100 as shown in FIGS. 14A-14E. The prior art shock wave head 43 was placed externally on the skull and transmit the emitted shock wave patterns through the skin, cranial bone tissue 116 for example and then into the adjacent brain tissue 100 to be treated, as shown in FIG. 13B. In that case of extracorporeal non-invasive treatments of damaged brain tissue, preferably the outer skin tissue is pressed against the treatment region to insure the transmission loss was reduced. In some cases, the treatment zone may benefit or require numbing prior to treatments in advance of surgical procedures. This was particularly true when the use of high energy focused waves were being transmitted through bone tissue to stimulate the sensitive nerves in the treatment area as shown in FIG. 13B. Naturally, energy losses through the skull were high and unpredictable making the outcomes somewhat dubious. The present invention overcomes these issues by employing a new very compact in size applicator device 400 configured to easily fit inside the mouth. The allows the head 440 of the applicator device 400 to be positioned anywhere along the roof of the mouth and to transmit waves or pulses directly to the brain 100 as shown. This technique means thick boney structures like the skull 116 are avoided. This technique is a great improvement, but it also has issues like the region of the sinus cavities that, if in the path, must be addressed, as will be discussed later. Assuming the target area or site is within a projected area of the wave transmission, a single transmission dosage of wave energy may be used. The transmission dosage can be from a few seconds to 20 minutes or more dependent on the condition. Preferably the waves are generated from an unfocused or focused source. The unfocused waves can be divergent, planar or near planar and having low pressure amplitude and density in the range of 0.00001 mJ/mm$^2$ to 1.0 mJ/mm$^2$ or less, most typically below 0.25 mJ/mm$^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission. In treating some hard to penetrate regions, the pressure pulse more preferably is a high energy target focused wave pattern which can effectively penetrate through outer structures prior to being dampened while still exposing the brain tissue to activating pressure pulses or shock waves. This emitted energy preferably stimulates the cells without rupturing cellular membranes. The surrounding healthy cells in the region treated are activated initiating a defense mechanism response to assist in eradication of the unwanted infection or diseased tissue while stimulating new growth of brain cells.

Figure 14A:
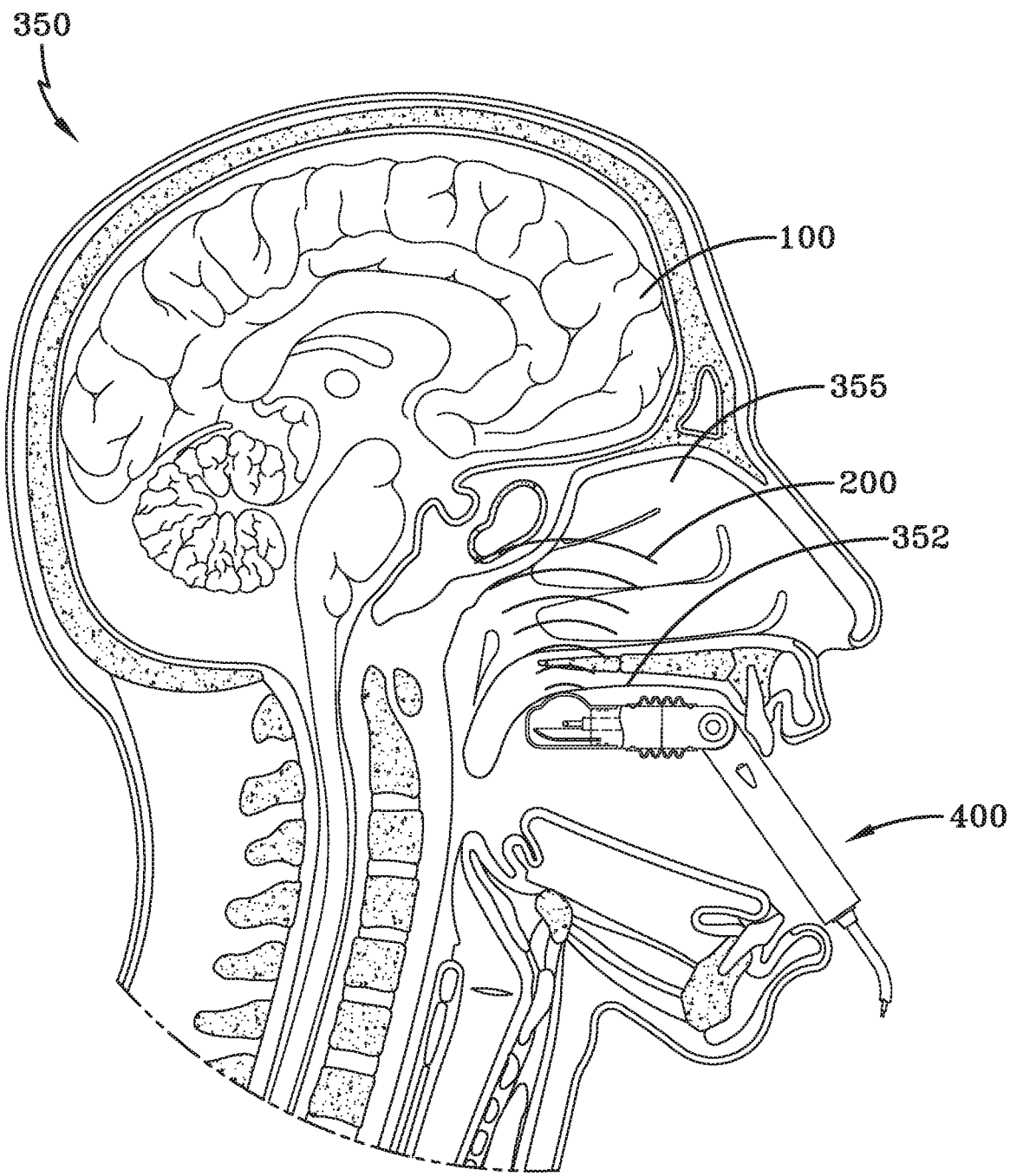
Figure 14B:
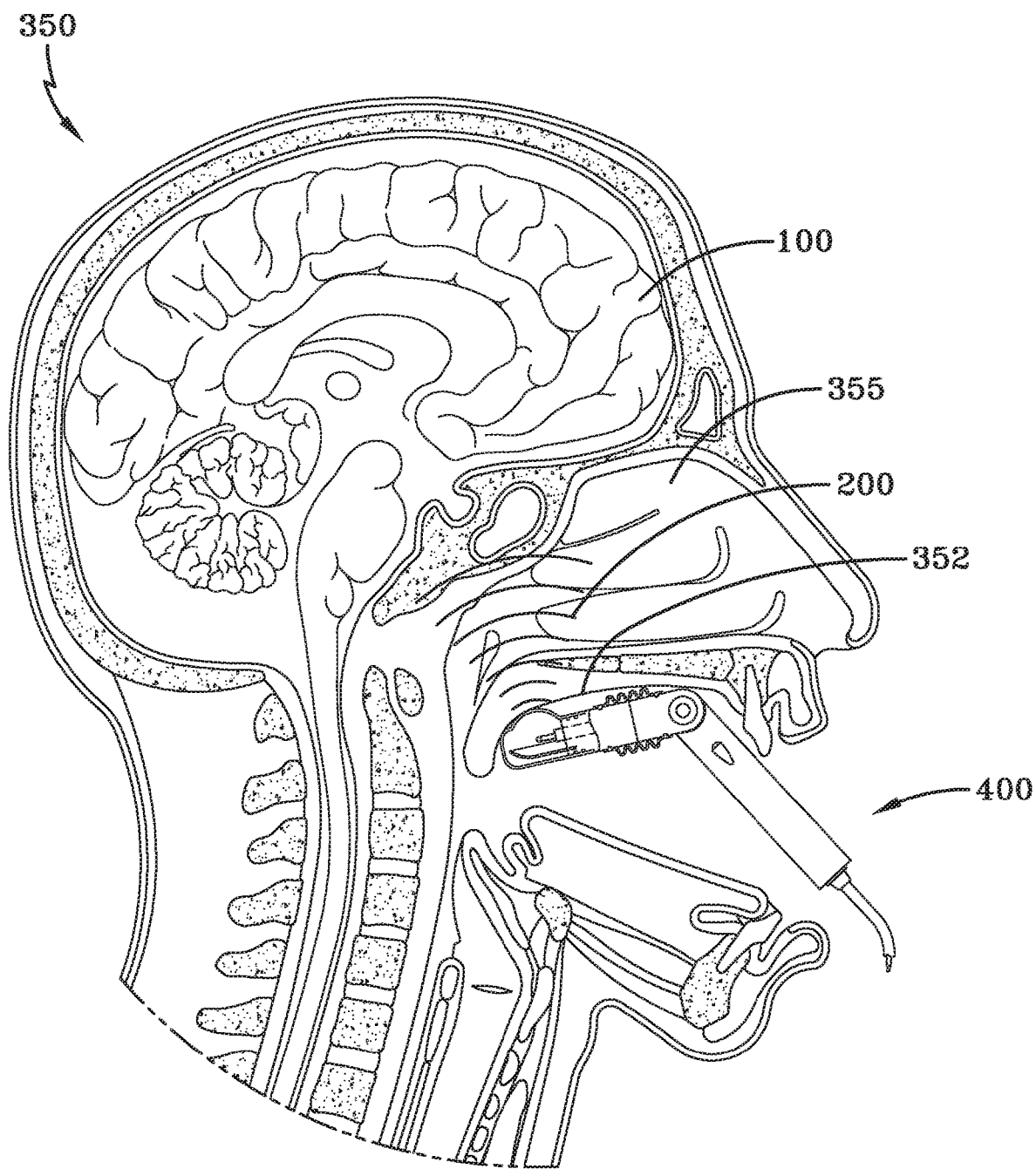
Figure 14C:
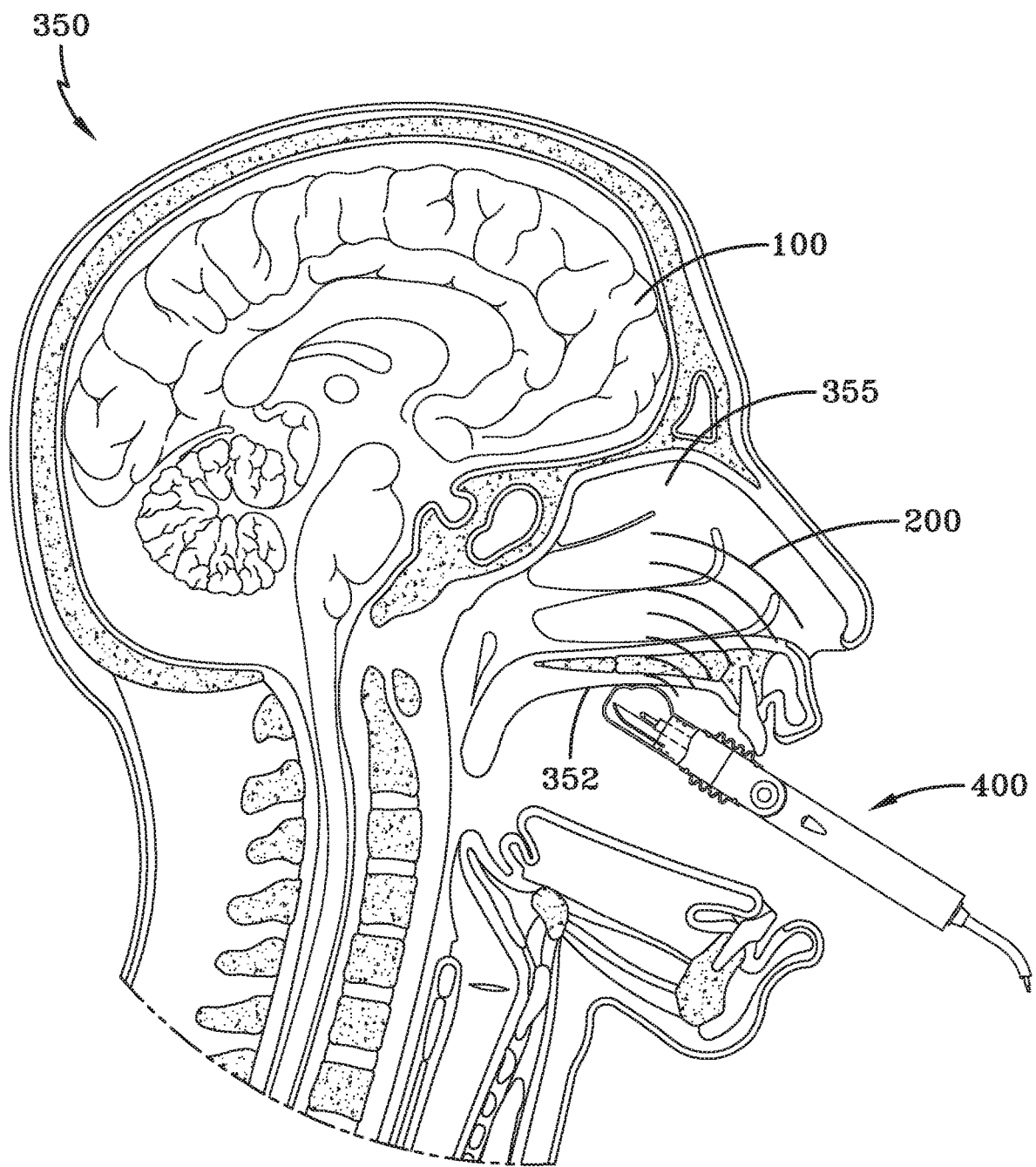
Figure 14D:
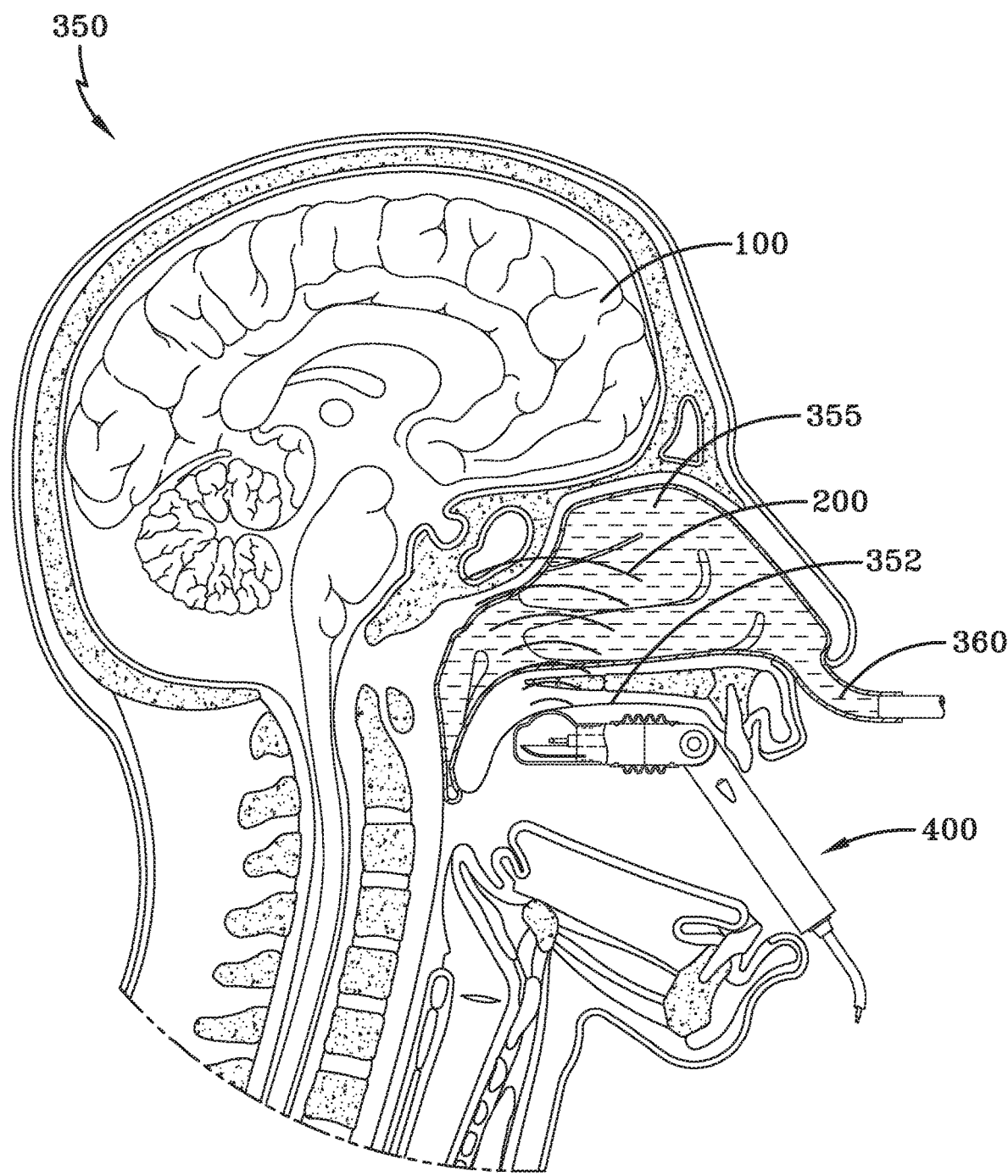

With reference to FIGS. 14A-14E, a cross sectional view of a patient's head 350 is illustrated. As shown in FIG. 14A, the handheld applicator device 400 is shown in a position in a rearward portion of the mouth 352 where the lens cover or membrane 450, 460 is pressing against the roof of the mouth 352 and the transmission of the shock waves or pressure pulses are directed upward through the roof of the mouth towards the brain 100 for a treatment. In this configuration, the handheld device 400 is bent such that it forms an obtuse angle with regard to the longitudinal axis of the body structure 410 main portion 420. With reference to FIG. 14B, the handheld device 400 is shown further positioned inside the mouth 352 towards the very rearward portion of the mouth opening and bent at an increased obtuse angle so the wave patterns are directed more towards the center of the brain 100. In FIG. 14C, when the handheld device 400 is in the straight position with the angle 8 at approximately 180 degrees relative to the longitudinal axis of the body structure 410 main portion 420. The device 400, even when tilted, will be directed through the sinus cavity 355 towards the nose and effectively would miss the brain. Accordingly, it is ideal for the handheld device 400 to be positioned as shown in FIGS. 14D and 14E towards the rear of the mouth opening. As shown in FIG. 14D, an alternative treatment methodology is used wherein a fillable bladder 360 is positioned within the sinus cavity 355 and is filled with a fluid. This facilitates the transmission of the acoustic waves or pressure pulses towards the brain 100 and eliminates any open cavities that tend to dampen or reduce the performance of the wave pattern, as it is well known that air dissipates sound and that the acoustic wave is best transmitted when there is a clear fluid coupling, as shown in FIG. 14D. FIG. 14E is an alternative method wherein the patient's nasal cavity 355 is illustrated filled with fluid. In this alternative embodiment, the handheld device 400 is similarly positioned to transmit the shock waves through the roof of the mouth 352, but as will be observed, the inflatable bladder 360 is replaced with a plug 361 at the nasal passages and an inflatable rear bladder 362 at the rearward portion away from the transmission of the wave forms. This inflatable rear bladder 362 can be filled with air and plug and seal the rearward portion of the sinus cavities 355 such that the fluid is entrapped in the patient's sinus cavities to make sure that the transmission wave pattern is not dampened or lost by voids created in the sinus cavities. Alternatively, though not shown, the patient could be inclined on a 45-degree angle with the patient's feet well above the patient's head, eliminating the need for blocking the drainage of fluid from the sinus cavities 355.

With reference to FIGS. 15A-18, a preferred embodiment of the handheld applicator device 400 of the present invention is illustrated. The device being a handheld applicator, has a longitudinal body structure or body 410 with a main portion 420 at the proximal end and a pivotable portion 430 for the doctor to hold while transmitting or emitting shock waves or pressure pulses through the patient's' roof of the mouth 352 towards the brain 100, as previously discussed. As shown, the body structure 410 is pivotally connected to the pivotable portion 430 and head structure 443 of the applicator head 440. The applicator head 440 is pivotally connected to the body structure 410 main portion 420 so that it can form any number of angles from 90 degrees to approximately 270 degrees affording the ability to manipulate the device 400 so that the wave forms can most easily be directed to the desired target location within the brain 100.

Figure 15A:
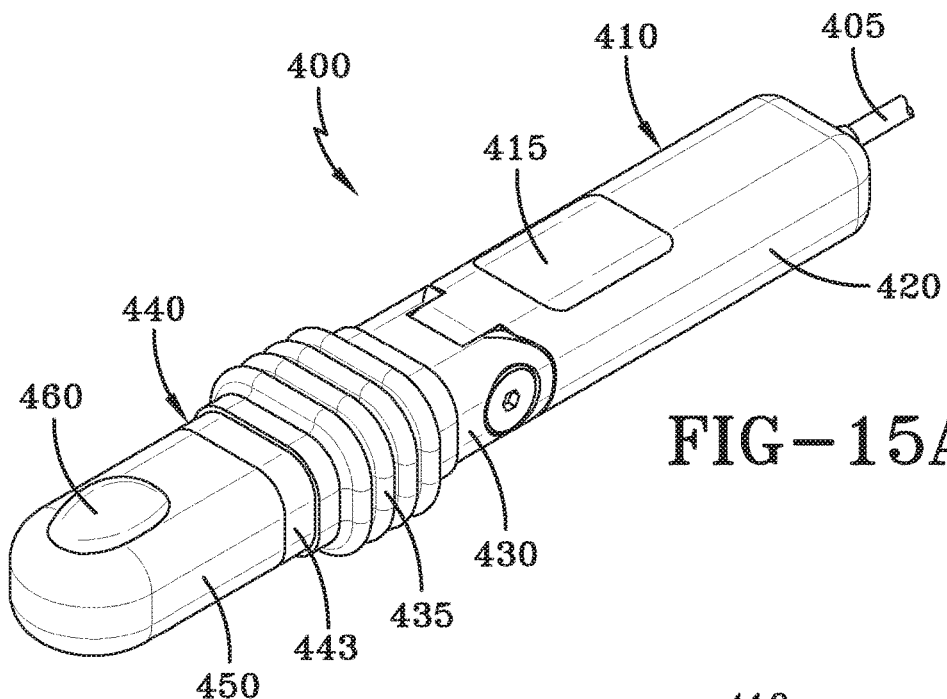
FIG. 15A is a perspective view of a first embodiment handheld device according to the present invention.
Figure 15B:
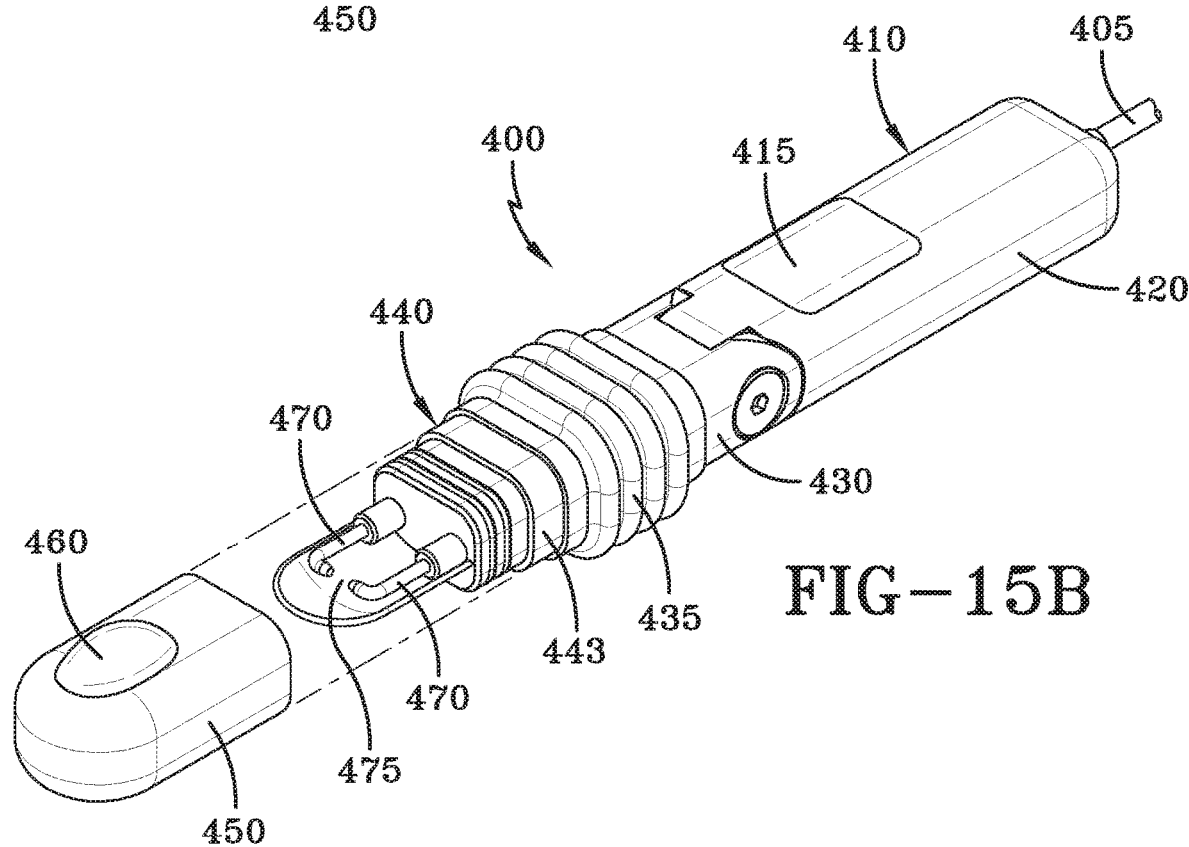
FIG. 15B is a perspective view taken from FIG. 15A with the lens or membrane shown removed exposing the electrode and reflector.
Figure 16A:
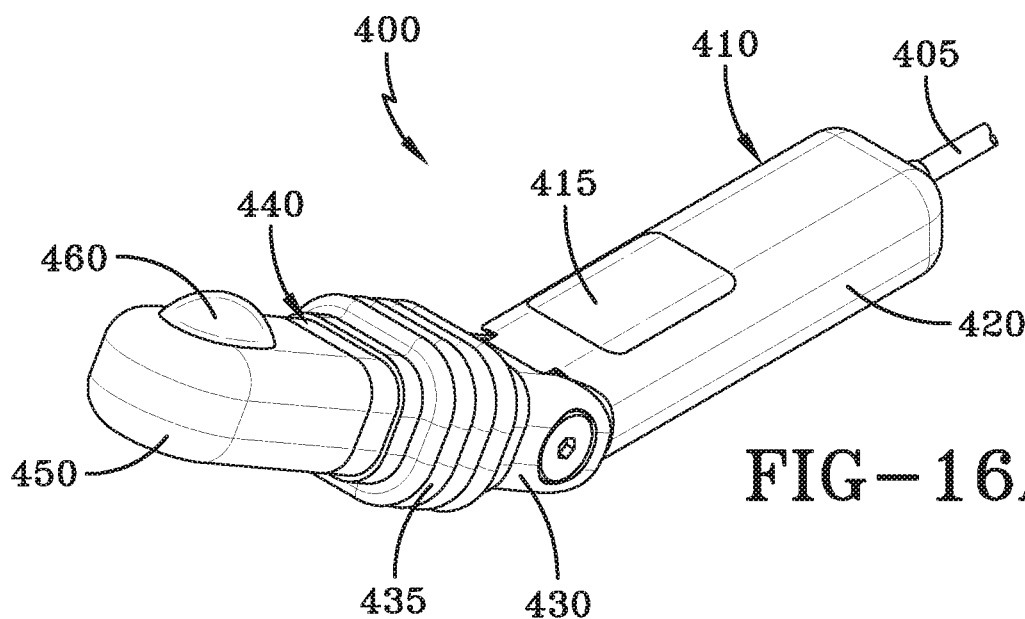
FIG. 16A is a view showing the device in a bent orientation with the head tilted upward at an angle θ of less than 90 degrees relative to the body structure.
Figure 16B:
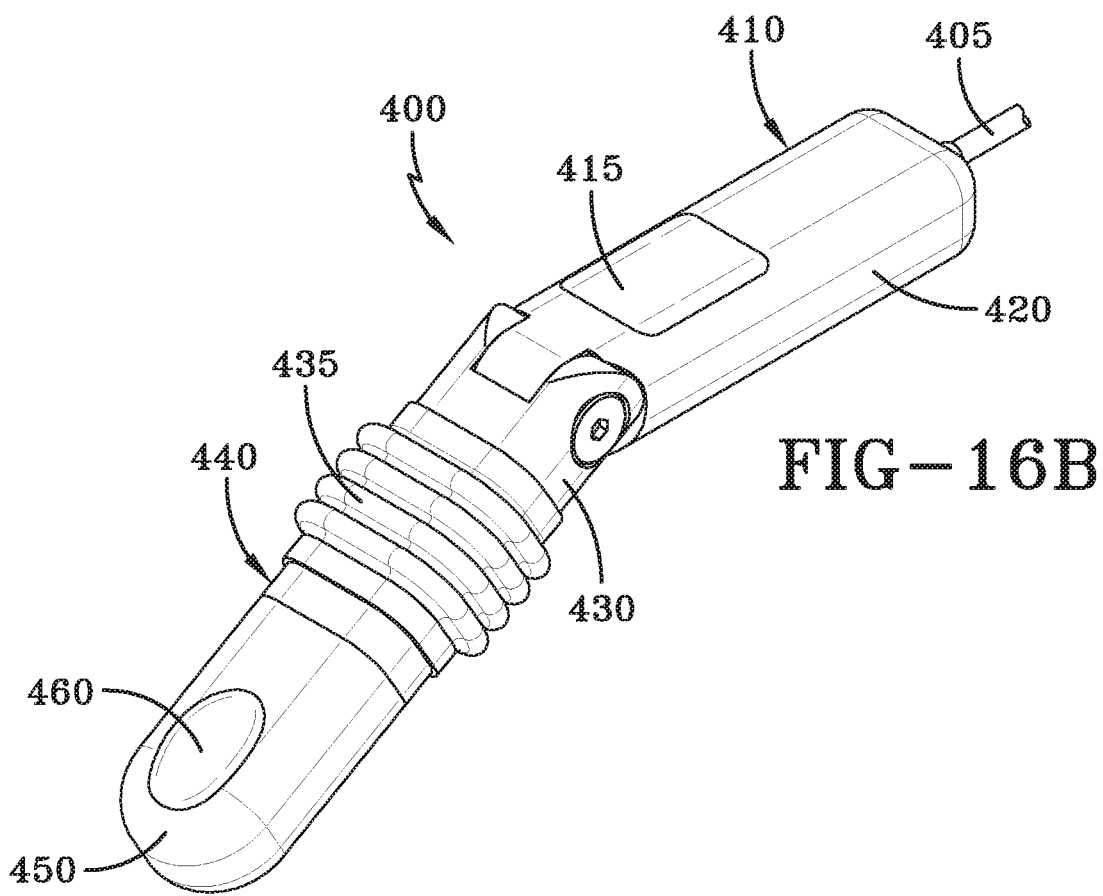
FIG. 16B is a similar view as FIG. 16A, but with the head tilted downwardly at al angle θ of greater than 90 degrees relative to the body structure.

As illustrated in FIGS. 15A and 15B, the distal end of the applicator device 400 shows an optional lens projection 460 on the lens cover or membrane 450, the lens cover or membrane 450 covering a pair of electrodes 470 and a reflector 445. The head structure 443 holds electrodes 470 that generate a spark in a gap 475 between the electrode tips 472, as illustrated in FIG. 15B. This gap 475 provides a space such that when power is transmitted to the electrodes 470 an electric spark is created. The reflector 445 then takes the shock waves or pressure pulses produced form this emission or activation of the electrodes 470 and transmits/ reflects those outwardly towards the bulbous end on the lens cover or membrane 450, 460 as illustrated. Preferably, in an electrohydraulic device, the lens cover or membrane 450 will be provided with and filled with a liquid fluid such as water such that the transmission of the acoustic shock wave is formed electrohydraulically. Alternatively, piezoelectric, spherical, ballistic or any number of shock wave producing elements can be used with the wave form preferably being directed towards the brain. As illustrated, the device 400 is extremely small and configured to fit easily within the mouth. As illustrated, there is an elastomeric boot 435 positioned along the applicator head 440 partially over the head structure 443 and pivotable portion 430. The lens or membrane covering fits snugly against the stepped portion of the applicator head 440 head structure 443 and is pressed on tightly to make a fluid tight seal such that when the applicator device 400 is activated, the fluid within the lens cover or membrane 450 is completely sealed away from the patient. The device 400 as shown in FIG. 16A and B is shown tilted at an angle 8, the angle 8, as discussed, preferably forms an obtuse angle 8 relative to the body structure of greater than 90 degrees up to substantially 270 degrees to provide easy access and positioning of the applicator head against the roof of the mouth 352.

Figure 17:
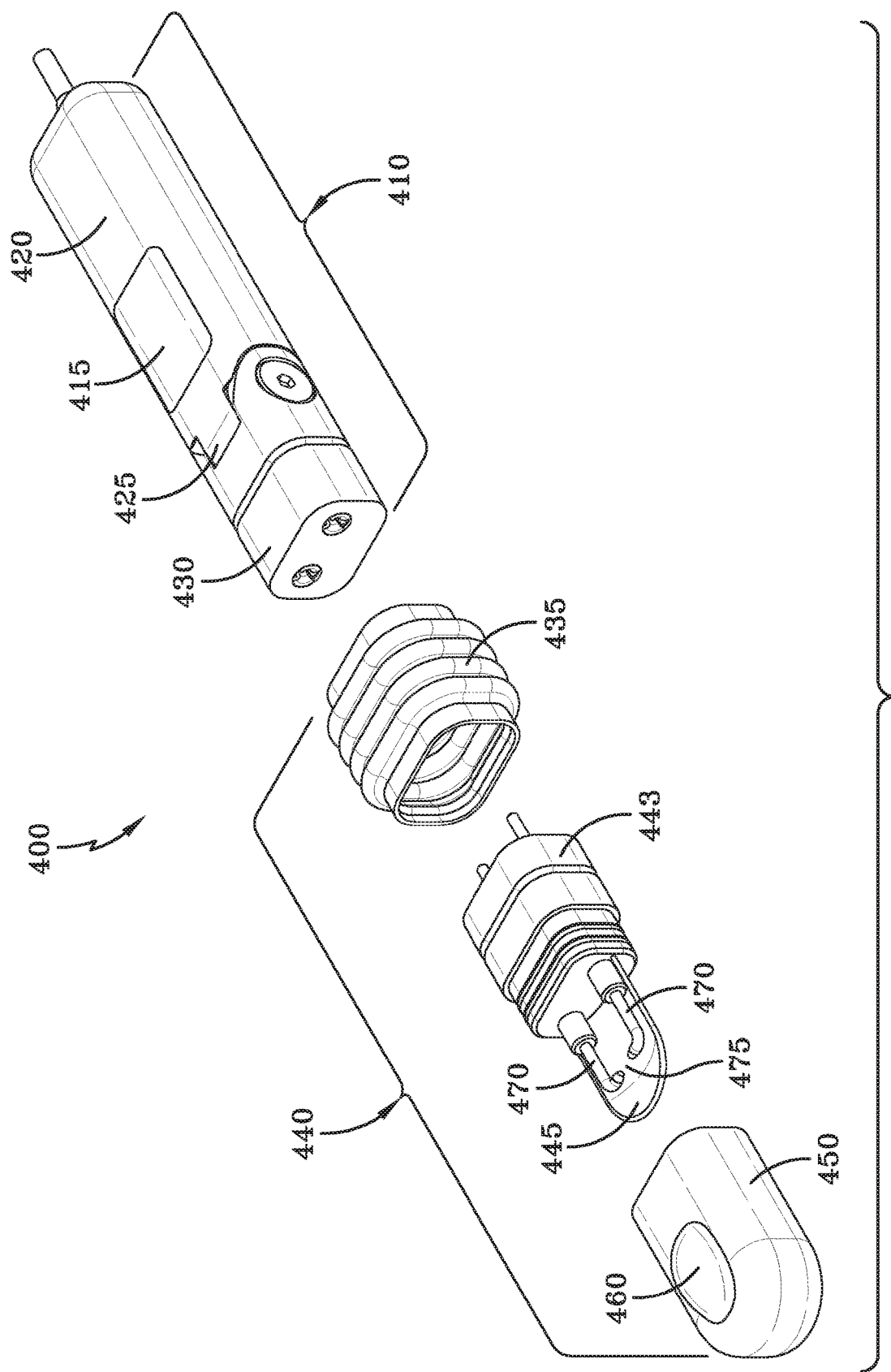
FIG. 17 shows an exploded view of the device of the first embodiment broken into subassemblies.

With reference to FIG. 17, the primary subassemblies of the applicator device 400 are illustrated. As shown, there is a cord 405 extending from a proximal end of the body structure main portion 420 of the device. The body structure 410 includes a pivotable portion 430 with a pair of receptacles 438 for receiving the ends of the electrodes 470 in the applicator head 440 head structure 443, as illustrated. These are electrically isolated such that when activated, a spark can be generated at the tips 472 as previously discussed. A boot 435 is provided to help encircle and seal the assembly of the head structure 443 to the pivotable portion 430. The lens cover or membrane 450 is shown at the distal end that will be used to transmit the acoustic shock waves or pressure pulses and to provide a smooth comfortable surface to be pressed against the roof of the mouth 352 to make a fluid coupling so that the transmission can be effectively provided with minimal transmission loss of acoustic energy or pressure pulse energy.

Figure 18:
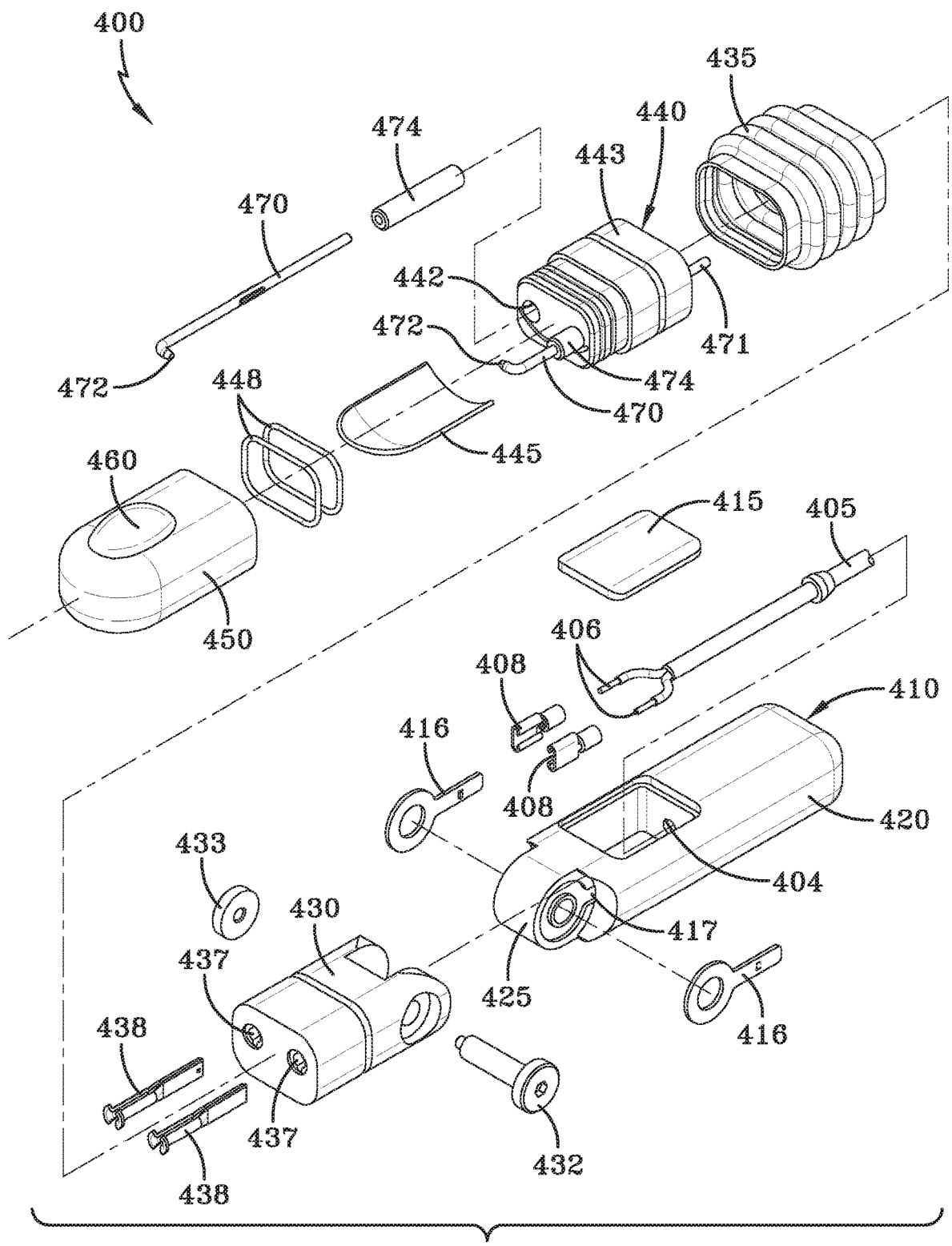
FIG. 18 shows an exploded view with the parts of all the subassemblies illustrated.

With reference to FIG. 18, a more detailed view of the components of the device 400 is illustrated. As shown in the lower portion of the figure, the electrical cord 405 is bifurcated into two portions 406 forming a "Y" shape with a pair of electrical couplings 408 crimped onto the portions 406. The electrical wiring is passed through an opening 404 in the body structure main portion 420 of the device 400. Once through the main portion 420, electrical couplings 408 can be crimped tightly onto the exposed wire ends 406, as illustrated. On each side of the pivoting connection 425 are a pair of electrical connections 416, these connections 416 will pass through a slot 417 and will be connected to the electrical couplings 408. A pivot pin 432 is provided in the pivotable portion 430 of the body structure 410 as illustrated. The pivotable portion 430 is connected to the body structure main portion 420 via the pin 432 and nut 433. When tightened down, the pivotable portion 430 can then be bent at any desired angle between 90 and 270 degrees, as previously discussed. The applicator head structure 443 and pivotable portion 430 have a pair of electrical connectors 438 that are slid through openings 437 that will make contact with the electrical connectors 416 completing the circuit. The electrodes 470 pass through an insulator sleeve 474 and into the openings 442 of the head structure 443. When so positioned, ends 471 of the electrodes 470 are exposed. Shown in the upper right is the boot 435 that will surround this subassembly when connected. Positioned on one side of the pair of electrodes 470 is a reflector 445. As illustrated, this reflector 445 has a parabolic structure. Any number of shapes can be used for the reflector 445, it is only important that the shape provides an optimal transmission of the wave form when the applicator device 400 is fired. A pair of O-rings 448 is shown that couple to the grooves 449 in the applicator device 400. These O-rings 448, when positioned, provide an air-tight seal for the membrane 450 which will preferably be filled with a fluid when the device 400 is used as an electrohydraulic shockwave applicator. As further shown in the longitudinal body structure 410 there is a cover 415 that will cover the electrical components once the device 400 is assembled.

Figure 19A:
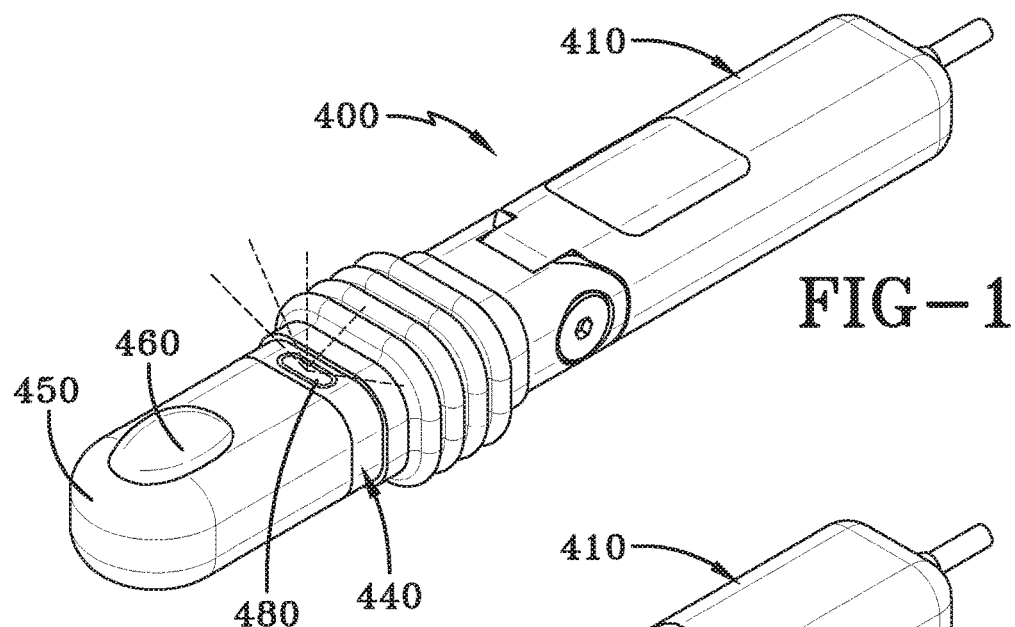
FIG. 19A is a perspective view showing an LED in an upper surface of the applicator head.
Figure 19B:
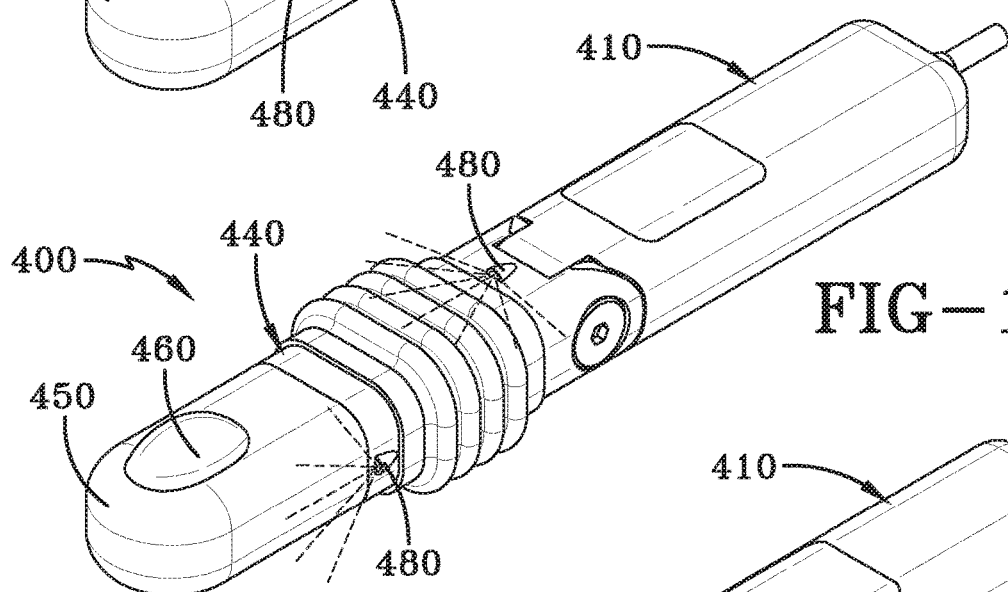
FIG. 19B is a perspective view of the device with multiple LED's, one positioned on a top and one or both sides of the device.
Figure 19C:
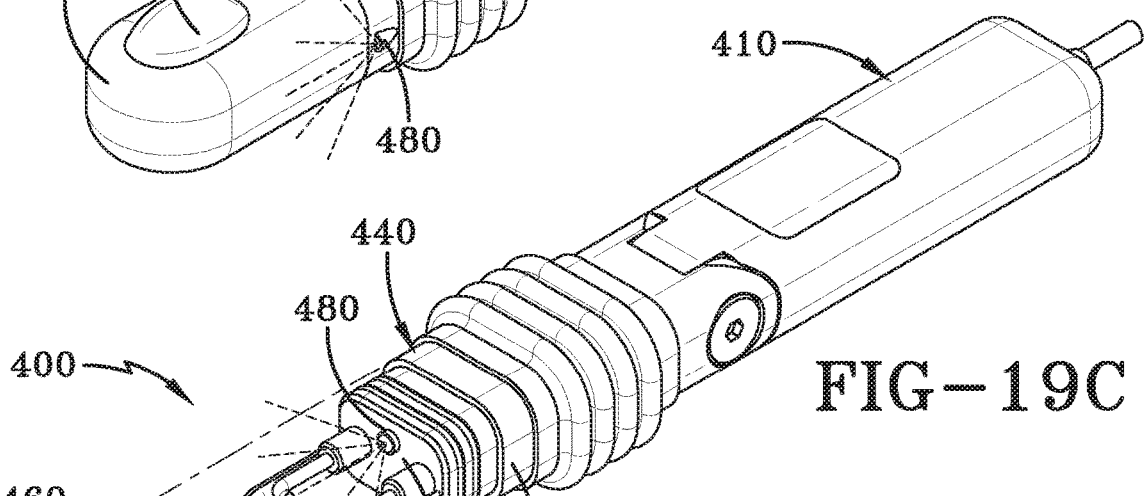
FIG. 19C is a perspective view of the device with an LED provided within the electrode chamber.

With reference to FIGS. 19A-19C, the device previously discussed, can be modified so that one or more LED lights 480 can be provided to illuminate the inside surface of the mouth 352. In FIG. 19A, this is shown as a simple flat portion, the LED 480 is shown in an upper surface of the applicator head 440. In FIG. 19B, the LED's 480 are positioned on a top and one or both sides of the device 400. In FIG. 19C, the LED 480 is provided within the electrode chamber 478 and the lens 460 or covering membrane 450 is preferably translucent or transparent such that the light can be easily seen by the operator.

As discussed, the present invention provides a unique way in which to provide acoustic shock waves or pressure pulses to a brain to be treated for any variety of diseases or conditions through an opening of the mouth.

These shock wave energy transmissions are effective in stimulating a cellular response and can be accomplished without creating the cavitation bubbles in the tissue of the target site when employed in other than site targeted high energy focused transmissions. This effectively ensures the brain tissue does not have to experience the sensation of hemorrhaging so common in the higher energy focused wave forms having focal point at or within the targeted treatment site. Bleeding internally causes an increase in fluid pressure which can lead to increased brain damage. This can be completely avoided in this treatment protocol.

The fact that some if not all of the dosage can be at a low energy the common problem of localized hemorrhaging is reduced making it more practical to administer multiple dosages of waves from various orientations inside the mouth to further optimize the treatment and cellular stimulation of the target site. Heretofore focused high energy multiple treatments induced pain and discomfort to the patient. The use of low energy focused or un-focused waves at the target site enables multiple sequential treatments.

The present method may need precise site location and can be used in combination with such known devices as ultrasound, cat-scan or x-ray imaging if needed. The physician's general understanding of the anatomy of the patient may be sufficient to locate the target area to be treated. This is particularly true when the device is visually within the surgeon's line of sight and this permits the lens or cover of the emitting shock wave source to impinge on the affected brain tissue directly through a transmission enhancing gel, water or fluid medium during the pressure pulse or shock wave treatment. The treated area can withstand a far greater number of shock waves based on the selected energy level being emitted. For example, at very low energy levels the stimulation exposure can be provided over prolonged periods as much as 20 minutes if so desired. At higher energy levels the treatment duration can be shortened to less thane minute, less than a second if so desired. The limiting factor in the selected treatment dosage is avoidance or minimization of surrounding cell hemorrhaging and other kinds of damage to the surrounding cells or tissue while still providing a stimulating stem cell activation or a cellular release or activation of proteins such as brain derived neurotropic factor (BDNF) or VEGF and other growth factors while simultaneously germicidally attacking the degenerative tissue or infectious bacteria at the target site.

Due to the wide range of beneficial treatments available it is believed preferable that the optimal use of one or more wave generators or sources should be selected on the basis of the specific application. A key advantage of the present inventive methodology is that it is complimentary to conventional medical procedures. In the case of any operative surgical procedure the surgical area of the patient can be bombarded with these energy waves to stimulate cellular release of healing agents and growth factors. This will dramatically reduce the healing process time. Most preferably such patients may be provided more than one such treatment with an intervening dwell time for cellular relaxation prior to secondary and tertiary post operative treatments.

The underlying principle of these pressure pulse or shock wave therapy methods is to enrich the treatment area directly and to stimulate the body's own natural healing capability. This is accomplished by deploying shock waves to stimulate strong cells in the surrounding tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly, not only can the energy intensity be reduced in some cases, but also the number of applied shock wave impulses can be lowered from several thousand to as few as one or more pulses and still yield a beneficial stimulating response. The key is to provide at least a sufficient amount of energy to activate healing reactions.

In clinical rat studies the remarkable re-growth of cut sciatic nerves has been demonstrated. The study involved cutting about 1.5 cm of the sciatic nerve, turning it 180° and suturing the cut ends back to the nerve (this model represents a nerve graft), closing the skin, followed by localized treatment using the present invention technology Co-inventor, Dr. Wolfgang Schaden, found that the nerves reattached/regenerated themselves better in cases where shock waves were applied. In addition, it was found that treated rats had a higher concentration of a certain protein in the brain that is common with well-trained rats (i.e. rats undergoing physiotherapy).

The trial was a 3 tailed study: 1st group of rats: dissection of the sciatic nerve and immediate microsurgical suture of the nerve. This was the control group. 2nd group: this group had the same procedure but after suturing the skin immediately shockwaves were applied. 3rd group: resection of 1.5 cm of the sciatic nerve and microsurgical suture upside-down (nerve graft model). After suturing the skin immediately shockwave therapy. Till now we have the following results: Group 1 had the expected results of sutured nerves (compared to historical study groups). Group 2 and even group 3 were clinically better than group 1. Group 2 and 3 were also better in electromyographical examinations. Both shockwave groups had significant higher levels of BDNF as the control group, but even higher levels than trained rats (based on historical comparison to trials that have been previously performed).

Dr. Robert Schmidhammer who performed the nerve trials in Austria found the protein he could prove to be produced in the brain of the rats of the shock wave therapy is called brain derived neurotropic factor (BDNF). The concentration of this protein in the shock wave treated rats was even higher than in trained rats.

These studies relied on the stimulation of the rats own natural healing ability after exposure to a shock wave treatment. The control group of rats had generally a failure to reattach and as expected no return of nerve function. This exposure to shock waves enhancing the neurological brain activity in the treated rats proves the overall systemic response of the nervous system to regenerative growth and repair after shock wave exposure at least on lower mammals such as rats.

This finding has led to the projected use of such treatments on humans for regenerative repair of degenerative conditions, the clinical studies so far indicating the same improvements can be anticipated in primates including humans.

The use of shock waves as described above appears to involve factors such as thermal heating, light emission, electromagnetic field exposure, chemical releases in the cells as well as a microbiological response within the cells. Which combination of these factors plays a role in stimulating neurological healing is not yet resolved. However, there appears to be a commonality in the fact that growth factors are released which the inventors find indicative that otherwise dormant cells within the nerve tissue appear to be activated which leads to the remarkable ability of the targeted area to generate new growth or to regenerate weakened vascular networks or blood circulation in for example to assist in brain tissue regeneration. This finding leads to a complimentary use of shock wave therapy in combination with stem cell therapies that effectively activate or trigger stem cells to more rapidly replicate enhancing the ability to harvest and culture more viable cells from the placenta, a nutrient culture of said stem cells, or other sources. The ability to stimulate stem cells can occur within the patient's own body activating the naturally occurring stem cells or stem cells that have been introduced to the patient as part of a treatment beneficially utilizing stem cells. This is a significant clinical value in its own right.

In one embodiment, the invention provides for germicidal cleaning of diseased or infected areas and for wound cleaning generally after exposure to surgical procedures.

The use of shock wave therapy requires a fundamental understanding of focused and unfocused shock waves, coupled with a more accurate biological or molecular model.

Focused shock waves are focused using ellipsoidal reflectors in electromechanical sources from a cylindrical surface or by the use of concave or convex lenses. Piezoelectric sources often use spherical surfaces to emit acoustic pressure waves which are self-focused and have also been used in spherical electromagnetic devices.

The biological model proposed by co-inventor Wolfgang Schaden provides a whole array of clinically significant uses of shock wave therapy.

Accepting the biological model as promoted by W. Schaden, the peak pressure and the energy density of the shock waves can be lowered dramatically. Activation of the body's healing mechanisms will be seen by in growth of new blood vessels and the release of growth factors.

The biological model motivated the design of sources with low pressure amplitudes and energy densities. First: spherical waves generated between two tips of an electrode; and second: nearly even waves generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern a planar or a nearly planar wave pattern and can be used in isolation or in combination with focused wave patterns yielding to an improved therapeutic treatment capability that is non-invasive with few if any disadvantageous contraindications. Alternatively, a focused wave emitting treatment may be used wherein the focal point extends preferably beyond the target treatment site, potentially external to the patient. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This ensures less tissue trauma while ensuring cellular stimulation to enhance the healing process and control the migration or spreading of the infection within the host The unfocused shock waves can be of a divergent wave pattern, planar or near planar pattern preferably convergent diffused or far-sighted wave pattern, of a low peak pressure amplitude and density. Typically, the energy density values range as low as 0.000001 mJ/mm$^2$ and having a high-end energy density of below 1.0 mJ/mm$^2$, preferably 0.20 mJ/mm$^2$ or less. The peak pressure amplitude of the positive part of the cycle should be above 1.0 and its duration is below 1-3 microseconds.

The treatment depth can vary from the surface to the full depth of the treated organ. The treatment site can be defined by a much larger treatment area than the 0.10-3.0 cm$^2$ commonly produced by focused waves. The above methodology is particularly well suited for surface as well as sub-surface soft tissue organ treatments like the brain.

The above methodology is valuable in generation of brain tissue, vascularization and may be used in combination with stem cell therapies as well as regeneration of damaged neurological tissue and vascularization.

The methodology is useful in stimulating enforcement of defense mechanisms in tissue cells to fight infections from bacteria and can be used germicidally to treat or cleanse wounds or other infected or degenerative target sites which is a primary concern in the case of treating human neurological diseases such as Alzheimer's disease, Parkinson's or ALS, resulting from such exposures to infectious or degenerative type agents.

While the above listed indications cited above are not exhaustive nor intended to be limiting, it is exemplary of the wide range of beneficial uses of high energy focused or low energy and amplitude unfocused divergent, planar or nearly planar shock waves, convergent shock waves, diffused shock waves or a combination of shock wave types in the treatment of humans and other mammals that are exposed to a neurological trauma or disease affecting the nervous system or are at high risk to be so exposed as the result of a high potential genetic pre-disposition to such diseases.

According to Dr. Lue, "Growing evidence suggests that BDNF expression is changed in various neuropsychiatric disorders. There may be a correlation between low BDNF levels and bipolar disorder, the emergence of depression, and schizophrenia. Therefore, BDNF levels should be considered as a transdiagnostic marker for psychiatric disorder activity. In conclusion, Li-ESWT may stimulate the expression of BDNF through the activation of the PERK/ATF4 signaling pathway."

A most significant method of preventive medicine can be practiced that is fully enabled by the use of these relatively low amplitude and pressure shock waves. The method includes the steps of identifying high risk patients for a variety of potential risk conditions. Such condition could be by way of example, any degenerative neurological disease or loss of feeling or circulation in a target region. After identifying a risk prone candidate providing one or a series of two or more exposure treatments with focused or unfocused, divergent, planar or near planar shock waves or convergent far-sighted focused shock waves or diffused shock waves to the treatment site, in this example the region surrounding or in proximity to an occurrence risk location. Then after treatments the physician can optionally ultrasound visually or otherwise determine the increase in regeneration or vascularization in the treated tissue after a period of time. Assuming an initial baseline determination of the neurological cell or nerve tissue regeneration or vascularization had been initially conducted an estimate or calculation of dosage requirements can be made. This procedure can be used for any at risk condition. After a surgical repair procedure, the surrounding tissues can be post-operatively shock wave treated as well.

The implications of using the (re)generative features of this type of shockwave therapy are any weakened organ or tissue can be strengthened to the point of reducing or eliminating the risk of irreparable damage or failure as a result of microbial infections or genetic pre-disposition.

The stimulation of growth factors and activation of healing acceleration within the cells of the treated tissues is particularly valuable to host patients and other high risk factor subjects wherein conventional treatments have been unsuccessful.

Even more striking as mentioned earlier, early prevention therapies can be employed to stimulate tissue or organ modeling to be maintained within acceptable ranges prior to an exposure to a degenerative failure. This is extremely valuable in the prevention of spreading the infection or degenerative condition for example. The methods would be to identify at risk patients with a known exposure risk and subjecting that patient to therapeutic shock wave therapy for the purpose of stimulating neurological tissue repair or regeneration effectively remodeling the patient's susceptible organs to be within accepted functional parameters prior to irreparable degeneration. The objective being to preventively stimulate cellular tissue repairs to preemptively avoid a degenerative condition from occurring which may result in the onset of a degenerative condition which can require invasive surgical procedures.

This preventive therapy is most needed to combat conditions which left untreated results in cellular destruction or any other degenerative conditions Furthermore, such acoustic shock wave forms can be used in combination with drugs, chemical treatments, irradiation therapy or even physical therapy and when so combined the stimulated cells will more rapidly assist the body's natural healing response and thus overcomes the otherwise potentially tissue damaging effects of these complimentary procedures.

The present invention provides an apparatus for an effective treatment of indications, which benefit from high or low energy pressure pulse/shock waves having focused or unfocused, nearly plane, convergent or even divergent characteristics. With an unfocused wave having nearly plane, plane, convergent wave characteristic or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm$^2$ or even as low as 0.000 001 mJ/mm$^2$. In a preferred embodiment, those low-end values range between 0.1-0.001 mJ/mm$^2$. With these low energy densities, side effects are reduced and the dose application is much more uniform. Additionally, the possibility of harming surface tissue is reduced when using an apparatus of the present invention that generates unfocused waves having planar, nearly plane, convergent or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output. Nevertheless, in some cases the first use of a high energy focused shock wave targeting the biomass or tumor may be the best approach to weaken the outer barrier of the shield of the biomass followed by a transmission of lower energy unfocused wave patterns, the combination being the most effective in germicidal destruction of the tumorous masses.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

The use of acoustic shock waves to patients exposed to neurological infections or nerve trauma stimulates a cellular response of the treated tissues as well as a cellular response in the surrounding tissue. This response activates otherwise dormant cells to increase the body's own defense mechanisms, allowing the cells to limit the migration of the infection and resultant tissue damage, but also to initiate the healing process. This feature means that the treating physician has the added benefit of a patient whose body will be strengthened to mitigate damage to otherwise healthy tissues and organs.

The nature of infectious disease treatments employing only antibiotics to kill infections is well known to actually make microorganisms mutate making them even harder to kill. The result is the patient is in a greatly weakened state overall. These mutant strains are so severe that the common antibiotic treatments are losing their ability to stop the spread of some infections which is well documented. These symptoms are generally reversible. The more serious complications may not be reversible. These antibiotic treatments can be cumulative in their adverse reactions and thus the effective treatment of the infections can also permanently damage otherwise healthy tissue and organs. The use of the shock waves as described above stimulates these healthy cells to defend against this spill over intrusion.

This means the physician can use these antibiotic treatments with far less adverse reactions if he combines the treatments with one or more exposures to acoustic shock waves either before introducing chemical antibiotic agents or shortly thereafter or both. This further means that the patient's recovery time should be greatly reduced because the patient treated with shock waves will have initiated a healing response that is much more aggressive than heretofore achieved without the cellular stimulation provided by pressure pulse or shock wave treatments. The current use of medications to stimulate such cellular activity is limited to absorption through the bloodstream via the blood vessels. Acoustic shock waves stimulate all the cells in the region treated activating an almost immediate cellular release of infection fighting and healing agents. Furthermore, as the use of otherwise conflicting chemicals is avoided, adverse side effects can be limited to those medicaments used to destroy the infectious cells. In other words the present invention is far more complimentary to such antibiotic treatments in that the stimulation of otherwise healthy cells will greatly limit the adverse and irreversible effects on the surrounding non-infected tissues and organs.

A further benefit of the use of acoustic shock waves is there are no known adverse indications when combined with the use of other medications or drugs. In fact, the activation of the cells exposed to shock wave treatments only enhances cellular absorption of such medication making these drugs faster acting than when compared to non-stimulated cells. As a result, it is envisioned that the use of one or more medicaments prior to, during or after subjecting the patient to acoustic shock waves will be complimentary to the treatment or pre-conditioning treatment for nerve damage. It is further appreciated that certain drug therapies can be altered or modified to lower risk or adverse side effects when combined with a treatment involving acoustic shock waves as described above.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

The invention claimed is:

1. A method of treating a brain using pressure pulses or shock waves comprises the steps of:
   inserting an applicator head of an acoustic shock wave generator or pressure pulse generator inside a mouth;
   coupling the applicator head directly or indirectly to an exposed surface of a palate;
   activating the acoustic shock wave generator to emit acoustic shock waves or the pressure pulse generator to emit pressure pulses through the palate to the brain; and
   filling nasal sinus cavities of a patient with a fluid and preventing fluid drainage by inclining the patient with the patient's feet above the patient's head or by placing a fluid filled bladder positioned into the nasal sinus cavities of the patient.

2. The method of claim 1 further comprises the step of:
   plugging or sealing said nasal sinus cavities to prevent fluid drainage while allowing the patient to breathe through the mouth.

3. The method of claim 2 wherein the emitted pressure pulses or acoustic shock waves are transmitted in a pattern passing through the fluid filled nasal sinus cavities to the brain.

4. The method of claim 3 wherein the emitted pressure pulses or acoustic shock waves pattern impinges the brain prior to a boney structure of the cranium or skull.

5. The method of claim 4 further comprising a step of subjecting the brain to convergent, divergent, planar or near planar acoustic shock waves or pressure pulses in an absence of a focal point impinging neuronal cells stimulating a cellular response in an absence of creating cavitation bubbles evidenced by not experiencing a sensation of hemorrhaging caused by the emitted waves or pulses in the neuronal cells; wherein an unobstructed path of the emitted shock waves or pressure pulses impinging the neuronal cells have no localized geometric focal volume or point of the emitted shock waves or pressure pulses; wherein the emitted shock waves or pressure pulses either have no geometric focal volume or point or have a focal volume or point ahead of the neuronal cells or beyond the neuronal cells thereby passing the emitted waves or pulses through the neuronal cells while avoiding having any localized focal point within the neuronal cells of the brain.

6. The method of claim 5 further comprising a step of subjecting the brain directly to the acoustic shock waves or pressure pulses having a low energy density of less than 1.0 mJ/mm$^2$ per shock wave stimulates said neuronal cells, wherein a path of the emitted pressure pulses or acoustic shock waves in the absence of any focal point or if a focal point exists, is positioned away from the neuronal cells being stimulated.

7. The method of claim 6 wherein the energy density is selected to avoid any cell damage to the neuronal cells or brain tissue.

8. The method of claim 1 wherein the pressure pulse or the shock wave is an acoustic pulse which includes several cycles of positive and negative pressure.

9. The method of claim 8 wherein the pressure pulse has an amplitude of a positive part of each of the several cycles above 0.1 MPa and a time duration of the pressure pulse is from below a microsecond to about a second.

10. The method of claim 9 wherein a rise time of a positive part of a first pressure cycle of the several cycles is in a range of nano-seconds (ns) up to milli-seconds (ms).

11. The method of claim 8 wherein the acoustic shock waves are pressure pulses having amplitudes above 0.1 MPa and rise times of the amplitude being below 1000 ns.

12. The method of claim 11 wherein the duration of a shock wave of the acoustic shock waves is below 1-3 micro-seconds (µs) for a positive part of each of the several cycles and above micro-seconds for a negative part of each of the several cycles.

13. The method of claim 1 wherein the emitted pressure pulses or shock waves are convergent, divergent, planar or near planar and the pressure pulse generator or acoustic shock wave generator is based on electro-hydraulic, electromagnetic, piezoceramic or ballistic wave generation having an energy density value ranging from a low end of 0.00001 mJ/mm$^2$ to a high end of below 1.0 mJ/mm$^2$.

14. The method of claim 1 further comprising the step of treating the brain to stimulate by accelerating or increasing neuronal cell growth or regeneration, wherein a step of administering is applied to a patient who has a pathological condition of the brain exhibiting damage caused by injury or disease including one of diabetes, brain damage associated with stroke, or for treating neurological disorders related to neurodegeneration, including Parkinson's disease, Alzheimer's disease and amyotrophic lateral sclerosis, multiple sclerosis and disseminated sclerosis, or for the treatment of mental disorders including bipolar disorder, depression, and schizophrenia.

15. The method of treating the brain of claim 1 stimulates neuronal cells or neurological brain tissue by accelerating and increasing neuronal cell growth or neurological brain tissue growth or regeneration or repair and wherein the neuronal cells or neurological brain tissue is from a mammal which is a human or an animal.

* * * * *